US012636084B2

(12) United States Patent
Chaoui et al.

(10) Patent No.: US 12,636,084 B2
(45) Date of Patent: May 26, 2026

(54) METHODS, SYSTEMS AND DEVICES FOR PRE-OPERATIVELY PLANNED SHOULDER SURGERY GUIDES AND IMPLANTS

(71) Applicant: Stryker European Operations Limited, Carrigtwohill (IE)

(72) Inventors: Jean Chaoui, Lyons (FR); Gilles Walch, Lyons (FR)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/934,874

(22) Filed: Nov. 1, 2024

(65) Prior Publication Data

US 2025/0057599 A1     Feb. 20, 2025

Related U.S. Application Data

(60) Continuation of application No. 17/874,452, filed on Jul. 27, 2022, now Pat. No. 12,133,691, which is a
(Continued)

(51) Int. Cl.
    *A61B 34/10*        (2016.01)
    *A61B 17/17*        (2006.01)
             (Continued)

(52) U.S. Cl.
    CPC .......... *A61B 34/10* (2016.02); *A61B 17/1739* (2013.01); *A61B 17/1778* (2016.11); *A61F 2/4014* (2013.01); *A61F 2/4081* (2013.01);

*G16H 40/63* (2018.01); *G16H 50/50* (2018.01); *A61B 2017/00526* (2013.01);
(Continued)

(58) Field of Classification Search
    CPC ............ A61B 17/1739; A61B 17/1778; A61B 17/1742; A61B 17/1746; A61B 2017/00526; A61B 2034/101; A61B 2034/104; A61B 2034/108; A61B 34/10
See application file for complete search history.

(56) References Cited

U.S. PATENT DOCUMENTS

| | | | |
|---|---|---|---|
| 5,370,692 A | 12/1994 | Fink et al. | |
| 5,725,586 A | 3/1998 | Sommerich | |
| | (Continued) | | |

FOREIGN PATENT DOCUMENTS

| | | | |
|---|---|---|---|
| CA | 3203261 A1 | 7/2022 | |
| EP | 2324801 A1 | 5/2011 | |
| | (Continued) | | |

OTHER PUBLICATIONS

Extended Search Report from counterpart European Application No. 25154176.9 dated Jul. 18, 2025, 7 pp.
(Continued)

*Primary Examiner* — Samuel S Hanna
(74) *Attorney, Agent, or Firm* — Shumaker & Sieffert, P.A.

(57) ABSTRACT

Methods, systems and devices for pre-operatively planned shoulder surgery guides and implants. Pre-operative planning methods for designing a shoulder surgery guide based on considerations of multiple factors affecting the outcome of shoulder surgery. Methods of using surgery guides and implants in patients undergoing shoulder surgery.

9 Claims, 7 Drawing Sheets

Related U.S. Application Data division of application No. 17/229,111, filed on Apr. 13, 2021, now Pat. No. 11,399,894, which is a continuation of application No. 16/918,347, filed on Jul. 1, 2020, now Pat. No. 12,070,272, which is a division of application No. 15/028,497, filed as application No. PCT/IB2014/002819 on Oct. 10, 2014, now Pat. No. 10,736,697.

(60) Provisional application No. 61/889,213, filed on Oct. 10, 2013.

(51) Int. Cl.

| *A61F 2/40* | (2006.01) |
| *G16H 40/63* | (2018.01) |
| *G16H 50/50* | (2018.01) |
| *A61B 17/00* | (2006.01) |
| *G06F 30/00* | (2020.01) |

(52) U.S. Cl.

CPC ... *A61B 2034/101* (2016.02); *A61B 2034/104* (2016.02); *A61B 2034/108* (2016.02); *G06F 30/00* (2020.01)

(56) References Cited

U.S. PATENT DOCUMENTS

| | | | |
|---|---|---|---|
| 6,459,948 B1 | 10/2002 | Ateshian et al. |
| 6,699,289 B2 | 3/2004 | Iannotti |
| 6,772,026 B2 | 8/2004 | Bradbury et al. |
| 6,944,518 B2 | 9/2005 | Roose |
| 7,468,075 B2 | 12/2008 | Lang et al. |
| 7,542,791 B2 | 6/2009 | Mire et al. |
| 7,618,451 B2 | 11/2009 | Berez et al. |
| 7,747,305 B2 | 6/2010 | Dean et al. |
| 7,799,077 B2 | 9/2010 | Lang et al. |
| 7,837,621 B2 | 11/2010 | Krause et al. |
| 7,981,158 B2 | 7/2011 | Fitz et al. |
| 7,983,777 B2 | 7/2011 | Melton et al. |
| 8,062,302 B2 | 11/2011 | Lang et al. |
| 8,105,330 B2 | 1/2012 | Fitz et al. |
| 8,160,325 B2 | 4/2012 | Zug et al. |
| 8,160,345 B2 | 4/2012 | Pavlovskaia et al. |
| 8,175,683 B2 | 5/2012 | Roose |
| 8,214,016 B2 | 7/2012 | Lavallee et al. |
| 8,221,430 B2 | 7/2012 | Park et al. |
| 8,231,634 B2 | 7/2012 | Mahfouz et al. |
| 8,337,501 B2 | 12/2012 | Fitz et al. |
| 8,337,507 B2 | 12/2012 | Lang et al. |
| 8,350,186 B2 | 1/2013 | Jones et al. |
| 8,377,073 B2 | 2/2013 | Wasielewski |
| 8,382,765 B2 | 2/2013 | Axelson et al. |
| 8,444,651 B2 | 5/2013 | Kunz et al. |
| 8,457,930 B2 | 6/2013 | Schroeder |
| 8,480,753 B2 | 7/2013 | Collazo et al. |
| 8,482,859 B2 | 7/2013 | Border et al. |
| 8,512,346 B2 | 8/2013 | Couture |
| 8,532,361 B2 | 9/2013 | Pavlovskaia |
| 8,532,806 B1 | 9/2013 | Masson |
| 8,532,807 B2 | 9/2013 | Metzger |
| 8,535,319 B2 | 9/2013 | Ball |
| 8,545,509 B2 | 10/2013 | Park et al. |
| 8,551,169 B2 | 10/2013 | Fitz et al. |
| 8,585,708 B2 | 11/2013 | Fitz et al. |
| 8,617,174 B2 | 12/2013 | Axelson, Jr. et al. |
| 8,617,242 B2 | 12/2013 | Philipp |
| 8,634,617 B2 | 1/2014 | Tsougarakis et al. |
| 8,634,618 B2 | 1/2014 | Zug et al. |
| 8,638,998 B2 | 1/2014 | Steines et al. |
| 8,682,052 B2 | 3/2014 | Fitz et al. |
| 8,709,089 B2 | 4/2014 | Lang et al. |
| 8,734,455 B2 | 5/2014 | Park et al. |
| 8,735,773 B2 | 5/2014 | Lang |
| 8,764,836 B2 | 7/2014 | De Wilde et al. |
| 8,775,133 B2 | 7/2014 | Schroeder |
| 8,777,875 B2 | 7/2014 | Park |
| 8,801,719 B2 | 8/2014 | Park et al. |
| 8,808,302 B2 | 8/2014 | Roose et al. |
| 8,830,233 B2 | 9/2014 | Friedland et al. |
| 8,843,229 B2 | 9/2014 | Vanasse et al. |
| 8,864,769 B2 | 10/2014 | Stone et al. |
| 8,864,834 B2 | 10/2014 | Boileau et al. |
| 8,884,618 B2 | 11/2014 | Mahfouz |
| 8,898,043 B2 | 11/2014 | Ashby et al. |
| 8,903,530 B2 | 12/2014 | Metzger |
| 8,932,361 B2 | 1/2015 | Tornier et al. |
| 8,934,961 B2 | 1/2015 | Lakin et al. |
| 8,971,606 B2 | 3/2015 | Chaoui et al. |
| 8,984,731 B2 | 3/2015 | Broeck et al. |
| 8,986,309 B1 | 3/2015 | Murphy |
| 8,989,460 B2 | 3/2015 | Mahfouz |
| 8,990,052 B2 | 3/2015 | Lavallee et al. |
| 8,992,538 B2 | 3/2015 | Keefer |
| 9,011,456 B2 | 4/2015 | Ranawat et al. |
| 9,020,788 B2 | 4/2015 | Lang et al. |
| 9,060,788 B2 | 6/2015 | Bollinger |
| 9,066,806 B2 | 6/2015 | Phipps |
| 9,084,617 B2 | 7/2015 | Lang et al. |
| 9,095,375 B2 | 8/2015 | Haimerl et al. |
| 9,107,679 B2 | 8/2015 | Lang et al. |
| 9,123,155 B2 | 9/2015 | Cunningham et al. |
| 9,138,258 B2 | 9/2015 | Geebelen |
| 9,180,015 B2 | 11/2015 | Fitz et al. |
| 9,186,161 B2 | 11/2015 | Lang et al. |
| 9,198,732 B2 | 12/2015 | Iannotti et al. |
| 9,204,977 B2 | 12/2015 | Bollinger |
| 9,220,516 B2 | 12/2015 | Lang et al. |
| 9,232,955 B2 | 1/2016 | Bonin, Jr. et al. |
| 9,237,950 B2 | 1/2016 | Hensley et al. |
| 9,278,413 B2 | 3/2016 | Sperling |
| 9,289,221 B2 | 3/2016 | Gelaude et al. |
| 9,295,482 B2 | 3/2016 | Fitz et al. |
| 9,301,812 B2 | 4/2016 | Kehres et al. |
| 9,308,091 B2 | 4/2016 | Lang |
| 9,320,608 B2 | 4/2016 | Sperling |
| 9,326,780 B2 | 5/2016 | Wong et al. |
| 9,345,548 B2 | 5/2016 | Schoenefeld et al. |
| 9,351,743 B2 | 5/2016 | Kehres et al. |
| 9,381,026 B2 | 7/2016 | Trouilloud et al. |
| 9,386,994 B2 | 7/2016 | Agnihotri et al. |
| 9,408,698 B2 | 8/2016 | Miles et al. |
| 9,414,928 B2 | 8/2016 | Sperling |
| 9,421,021 B2 | 8/2016 | Keppler |
| 9,451,973 B2 | 9/2016 | Heilman et al. |
| 9,498,132 B2 | 11/2016 | Maier-Hein et al. |
| 9,498,233 B2 | 11/2016 | Eash |
| 9,504,579 B2 | 11/2016 | Mahfouz et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,592,128 B2 | 3/2017 | Phipps |
| 9,597,201 B2 | 3/2017 | Bollinger |
| 9,615,834 B2 | 4/2017 | Agnihotri et al. |
| 9,615,840 B2 | 4/2017 | Iannotti et al. |
| 9,649,170 B2 | 5/2017 | Park et al. |
| 9,662,214 B2 | 5/2017 | Li et al. |
| 9,668,873 B2 | 6/2017 | Winslow et al. |
| 9,675,461 B2 | 6/2017 | Mahfouz |
| 9,681,925 B2 | 6/2017 | Azar et al. |
| 9,684,768 B2 | 6/2017 | Lavallee et al. |
| 9,693,785 B2 | 7/2017 | Theiss et al. |
| 9,713,533 B2 | 7/2017 | Taylor et al. |
| 9,713,539 B2 | 7/2017 | Haimerl et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,757,238 B2 | 9/2017 | Metzger |
| 9,763,682 B2 | 9/2017 | Bettenga |
| 9,775,680 B2 | 10/2017 | Bojarski et al. |
| 9,795,393 B2 | 10/2017 | Hughes et al. |
| 9,808,261 B2 | 11/2017 | Gelaude et al. |

(56) References Cited

U.S. PATENT DOCUMENTS

| | | | |
|---|---|---|---|
| 9,814,533 B2 | 11/2017 | Park et al. | |
| 9,820,868 B2 | 11/2017 | Witt et al. | |
| 9,839,438 B2 | 12/2017 | Eash | |
| 9,861,446 B2 | 1/2018 | Lang | |
| 9,895,230 B2 | 2/2018 | Mahfouz | |
| 9,913,691 B2 | 3/2018 | Brooks | |
| 9,925,048 B2 | 3/2018 | Winslow et al. | |
| 9,936,962 B2 | 4/2018 | Heilman et al. | |
| 9,937,046 B2 | 4/2018 | Mahfouz | |
| 9,980,780 B2 | 5/2018 | Lang | |
| 9,987,024 B2 | 6/2018 | Frey et al. | |
| 9,993,341 B2 | 6/2018 | Vanasse et al. | |
| 10,010,334 B2 | 7/2018 | Keppler | |
| 10,010,379 B1 | 7/2018 | Gibby et al. | |
| 10,010,431 B2 | 7/2018 | Eraly et al. | |
| 10,013,808 B2 | 7/2018 | Jones et al. | |
| 10,016,243 B2 | 7/2018 | Esterberg | |
| 10,016,811 B2 | 7/2018 | Neal | |
| 10,019,551 B2 | 7/2018 | Zellner et al. | |
| 10,022,137 B2 | 7/2018 | Theiss et al. | |
| 10,034,757 B2 | 7/2018 | Kovacs et al. | |
| 10,052,114 B2 | 8/2018 | Keppler et al. | |
| 10,052,170 B2 | 8/2018 | Saget et al. | |
| 10,052,206 B2 | 8/2018 | Mahfouz | |
| 10,092,419 B2 | 10/2018 | Hananouchi et al. | |
| 10,102,309 B2 | 10/2018 | McKinnon et al. | |
| 10,130,378 B2 | 11/2018 | Bryan | |
| 10,159,513 B2 | 12/2018 | Pavlovskaia et al. | |
| 10,172,715 B2 | 1/2019 | De Wilde et al. | |
| 10,182,870 B2 | 1/2019 | Park et al. | |
| 10,194,990 B2 | 2/2019 | Amanatullah et al. | |
| 10,195,036 B2 | 2/2019 | Ratron | |
| 10,195,043 B2 | 2/2019 | Taylor et al. | |
| 10,206,688 B2 | 2/2019 | Park et al. | |
| 10,213,311 B2 | 2/2019 | Mahfouz | |
| 10,251,755 B2 | 4/2019 | Boileau et al. | |
| 10,258,427 B2 | 4/2019 | Saget et al. | |
| 10,262,084 B2 | 4/2019 | Lavallee et al. | |
| 10,278,777 B1 | 5/2019 | Lang | |
| 10,292,768 B2 | 5/2019 | Lang | |
| 10,349,953 B2 | 7/2019 | Park et al. | |
| 10,368,947 B2 | 8/2019 | Lang | |
| 10,398,514 B2 | 9/2019 | Ryan et al. | |
| 10,405,927 B1 | 9/2019 | Lang | |
| 10,405,993 B2 | 9/2019 | Deransart et al. | |
| 10,413,416 B2 | 9/2019 | Boileau et al. | |
| 10,426,493 B2 | 10/2019 | Kehres et al. | |
| 10,426,495 B2 | 10/2019 | Bonin, Jr. et al. | |
| 10,426,549 B2 | 10/2019 | Kehres et al. | |
| 10,441,298 B2 | 10/2019 | Eash | |
| 10,463,497 B2 | 11/2019 | Sperling | |
| 10,499,996 B2 | 12/2019 | de Almeida Barreto | |
| 10,537,390 B2 | 1/2020 | Varadarajan et al. | |
| 10,543,100 B2 | 1/2020 | Couture et al. | |
| 10,546,423 B2 | 1/2020 | Jones et al. | |
| 10,548,667 B2 | 2/2020 | Flett et al. | |
| 10,548,668 B2 | 2/2020 | Furrer et al. | |
| 10,575,958 B2 | 3/2020 | Cardon et al. | |
| 10,580,217 B2 | 3/2020 | Jones et al. | |
| 10,600,515 B2 | 3/2020 | Otto et al. | |
| 10,603,113 B2 | 3/2020 | Lang | |
| 10,624,655 B2 | 4/2020 | Iannotti et al. | |
| 10,624,755 B2 | 4/2020 | Amis et al. | |
| 10,646,283 B2 | 5/2020 | Johnson et al. | |
| 10,646,285 B2 | 5/2020 | Siemionow et al. | |
| 10,650,594 B2 | 5/2020 | Jones et al. | |
| 10,660,709 B2 | 5/2020 | Chaoui | |
| 10,667,867 B2 | 6/2020 | Gangwar et al. | |
| 10,675,063 B2 | 6/2020 | Pavlovskaia et al. | |
| 10,687,901 B2 | 6/2020 | Thomas | |
| 10,722,310 B2 | 7/2020 | Luby | |
| 10,736,697 B2 | 8/2020 | Chaoui et al. | |
| 10,743,939 B1 | 8/2020 | Lang | |
| 10,762,623 B2 | 9/2020 | Geebelen et al. | |
| 10,818,199 B2 | 10/2020 | Buras et al. | |
| 10,825,563 B2 | 11/2020 | Gibby et al. | |
| 10,842,510 B2 | 11/2020 | Heilman et al. | |
| 10,842,512 B2 | 11/2020 | Bonin, Jr. et al. | |
| 10,846,851 B2 | 11/2020 | Boettger et al. | |
| 10,849,693 B2 | 12/2020 | Lang | |
| 10,861,236 B2 | 12/2020 | Geri et al. | |
| 10,888,378 B2 | 1/2021 | Walch | |
| 10,898,348 B2 | 1/2021 | Vivanz et al. | |
| 10,905,562 B2 | 2/2021 | Sbaiz et al. | |
| 10,912,571 B2 | 2/2021 | Pavlovskaia et al. | |
| 10,922,448 B2 | 2/2021 | McKinnon et al. | |
| 10,925,658 B2 | 2/2021 | Hopkins | |
| 10,973,535 B2 | 4/2021 | Iannotti et al. | |
| 10,973,580 B2 | 4/2021 | Berend et al. | |
| 10,987,190 B2 | 4/2021 | Flossmann et al. | |
| 11,013,560 B2 | 5/2021 | Lang | |
| 11,020,183 B2 | 6/2021 | Gomes | |
| 11,033,335 B2 | 6/2021 | Zhang | |
| 11,039,889 B2 | 6/2021 | Frey et al. | |
| 11,051,830 B2 | 7/2021 | Jaramaz et al. | |
| 11,062,522 B2 | 7/2021 | Jones et al. | |
| 11,071,592 B2 | 7/2021 | McGuan et al. | |
| 11,080,934 B2 | 8/2021 | Tseng et al. | |
| 11,083,525 B2 | 8/2021 | Varadarajan et al. | |
| 11,090,161 B2 | 8/2021 | Hodorek | |
| 11,103,311 B2 | 8/2021 | May et al. | |
| 11,129,678 B2 | 9/2021 | Park | |
| 11,134,963 B2 | 10/2021 | Buza et al. | |
| 11,135,016 B2 | 10/2021 | Frielinghaus et al. | |
| 11,141,276 B2 | 10/2021 | Kehres | |
| 11,153,555 B1 | 10/2021 | Healy et al. | |
| 11,166,733 B2 | 11/2021 | Neichel et al. | |
| 11,166,764 B2 | 11/2021 | Roh et al. | |
| 11,172,990 B2 | 11/2021 | Lang | |
| 11,172,996 B1 | 11/2021 | Qian et al. | |
| 11,176,750 B2 | 11/2021 | Jones et al. | |
| 11,179,249 B2 | 11/2021 | Deransart et al. | |
| 11,185,417 B2 | 11/2021 | Boileau et al. | |
| 11,202,675 B2 | 12/2021 | Uhde et al. | |
| 11,207,150 B2 | 12/2021 | Healy et al. | |
| 11,213,305 B2 | 1/2022 | Iannotti et al. | |
| 11,217,028 B2 | 1/2022 | Jones et al. | |
| 11,234,721 B2 | 2/2022 | Gargac et al. | |
| 11,237,627 B2 | 2/2022 | Gibby et al. | |
| 11,253,323 B2 | 2/2022 | Hughes et al. | |
| 11,278,299 B2 | 3/2022 | Neichel et al. | |
| 11,278,413 B1 | 3/2022 | Lang | |
| 11,287,874 B2 | 3/2022 | Gibby et al. | |
| 11,298,118 B1 | 4/2022 | Koo | |
| 11,298,140 B2 | 4/2022 | Wilkinson et al. | |
| 11,298,142 B2 | 4/2022 | Park et al. | |
| 11,298,188 B2 | 4/2022 | Kehres et al. | |
| 11,298,189 B2 | 4/2022 | Kelman et al. | |
| 11,302,005 B2 | 4/2022 | Tanji | |
| 11,311,341 B2 | 4/2022 | Lang | |
| 11,337,762 B2 | 5/2022 | McKinnon et al. | |
| 11,344,370 B2 | 5/2022 | Park et al. | |
| 11,357,576 B2 | 6/2022 | Jo et al. | |
| 11,382,699 B2 | 7/2022 | Wassall et al. | |
| 11,382,713 B2 | 7/2022 | Healy et al. | |
| 11,399,851 B2 | 8/2022 | Neichel et al. | |
| 11,399,894 B2 | 8/2022 | Chaoui et al. | |
| 11,410,769 B1 | 8/2022 | Mldirim | |
| 11,413,094 B2 | 8/2022 | Qiu et al. | |
| 11,419,618 B2 | 8/2022 | Kehres et al. | |
| 11,419,680 B2 | 8/2022 | Knotaxis et al. | |
| 11,432,931 B2 | 9/2022 | Lang | |
| 11,432,934 B2 | 9/2022 | Couture et al. | |
| 11,443,846 B2 | 9/2022 | Schoenefeld et al. | |
| 11,452,568 B2 | 9/2022 | Lang | |
| 11,457,982 B2 | 10/2022 | Marti et al. | |
| 11,461,983 B2 | 10/2022 | Jones et al. | |
| 11,471,303 B2 | 10/2022 | O'Grady | |
| 11,488,721 B2 | 11/2022 | Otto et al. | |
| 11,490,965 B2 | 11/2022 | Bischoff et al. | |
| 11,490,966 B2 | 11/2022 | Roche et al. | |
| 11,510,750 B2 | 11/2022 | Dulin et al. | |
| 11,532,135 B2 | 12/2022 | Geri et al. | |
| 11,559,403 B2 | 1/2023 | Kehres | |

(56) References Cited

U.S. PATENT DOCUMENTS

| | | | |
|---|---|---|---|
| 11,596,479 B2 | 3/2023 | McGuan et al. |
| 11,602,360 B2 | 3/2023 | Heilman et al. |
| 11,602,395 B2 | 3/2023 | Lang |
| 11,607,277 B2 | 3/2023 | Calloway et al. |
| 11,617,591 B2 | 4/2023 | Eash |
| 11,621,086 B2 | 4/2023 | Spanberg et al. |
| 11,622,818 B2 | 4/2023 | Siemionow et al. |
| 11,653,976 B2 | 5/2023 | Bonny et al. |
| 11,660,197 B1 | 5/2023 | Lang |
| 11,690,697 B2 | 7/2023 | Healy et al. |
| 11,696,833 B2 | 7/2023 | Casey |
| 11,712,302 B2 | 8/2023 | Walch |
| 11,717,412 B2 | 8/2023 | Cascy et al. |
| 11,730,497 B2 | 8/2023 | Iannotti et al. |
| 11,734,901 B2 | 8/2023 | Jones et al. |
| 11,737,883 B2 | 8/2023 | Metcalfe et al. |
| 11,751,946 B2 | 9/2023 | Gangwar et al. |
| 11,752,000 B2 | 9/2023 | Terill |
| 11,763,531 B2 | 9/2023 | Jones et al. |
| 11,766,268 B2 | 9/2023 | Iannotti et al. |
| 11,766,336 B2 | 9/2023 | Penninger et al. |
| 11,819,415 B2 | 11/2023 | Metcalfe et al. |
| 11,847,755 B2 | 12/2023 | Park et al. |
| 11,850,158 B2 | 12/2023 | Simoes et al. |
| 11,883,040 B2 | 1/2024 | Bonin, Jr. et al. |
| 12,070,272 B2 | 8/2024 | Chaoui et al. |
| 12,133,688 B2 | 11/2024 | Chaoui |
| 12,133,691 B2 | 11/2024 | Chaoui et al. |
| 12,137,982 B2 | 11/2024 | Chaoui et al. |
| 12,178,517 B2 | 12/2024 | Chaoui |
| 2001/0047210 A1 | 11/2001 | Wolf |
| 2002/0082741 A1 | 6/2002 | Mazumder et al. |
| 2004/0039259 A1 | 2/2004 | Krause et al. |
| 2004/0138754 A1 | 7/2004 | Lang et al. |
| 2004/0236424 A1 | 11/2004 | Berez et al. |
| 2004/0243481 A1 | 12/2004 | Bradbury et al. |
| 2005/0065617 A1 | 3/2005 | Moctezuma De La Barrera et al. |
| 2005/0065628 A1 | 3/2005 | Roose |
| 2005/0087047 A1 | 4/2005 | Farrar |
| 2005/0216305 A1 | 9/2005 | Funderud |
| 2006/0079963 A1 | 4/2006 | Hansen |
| 2006/0095047 A1 | 5/2006 | de la Barrera et al |
| 2006/0136058 A1 | 6/2006 | Pietrzak |
| 2006/0184454 A1 | 8/2006 | Ananda |
| 2007/0118055 A1 | 5/2007 | McCombs |
| 2007/0118243 A1 | 5/2007 | Schroeder et al. |
| 2007/0203605 A1 | 8/2007 | Melton et al. |
| 2007/0233141 A1 | 10/2007 | Park et al. |
| 2008/0269596 A1 | 10/2008 | Revie et al. |
| 2008/0269906 A1 | 10/2008 | Iannotti et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0089034 A1 | 4/2009 | Penney et al. |
| 2009/0216285 A1 | 8/2009 | Ek et al. |
| 2009/0276045 A1 | 11/2009 | Lang et al. |
| 2009/0318929 A1 | 12/2009 | Tornier et al. |
| 2010/0023015 A1 | 1/2010 | Park |
| 2010/0082035 A1 | 4/2010 | Keefer |
| 2010/0160917 A1 | 6/2010 | Fitz et al. |
| 2010/0222781 A1 | 9/2010 | Collazo et al. |
| 2010/0292963 A1 | 11/2010 | Schroeder |
| 2010/0303313 A1 | 12/2010 | Lang et al. |
| 2010/0305573 A1 | 12/2010 | Fitz et al. |
| 2010/0305574 A1 | 12/2010 | Fitz et al. |
| 2011/0029088 A1 | 2/2011 | Rausher et al. |
| 2011/0054478 A1 | 3/2011 | Vanasse et al. |
| 2011/0071802 A1 | 3/2011 | Bojarski et al. |
| 2011/0166661 A1 | 7/2011 | Boileau et al. |
| 2011/0190775 A1 | 8/2011 | Ure |
| 2011/0295329 A1 | 12/2011 | Fitz et al. |
| 2011/0304332 A1 | 12/2011 | Mahfouz |
| 2012/0041446 A1 | 2/2012 | Wong et al. |
| 2012/0041564 A1 | 2/2012 | Landon |

| | | | |
|---|---|---|---|
| 2012/0101503 A1 | 4/2012 | Lang et al. |
| 2012/0116203 A1 | 5/2012 | Vancraen et al. |
| 2012/0143267 A1 | 6/2012 | Iannotti et al. |
| 2012/0245647 A1 | 9/2012 | Kunz et al. |
| 2012/0276509 A1* | 11/2012 | Iannotti ............. A61B 17/1739 434/267 |
| 2012/0289965 A1 | 11/2012 | Gelaude et al. |
| 2012/0303035 A1 | 11/2012 | Geebelen |
| 2013/0018378 A1 | 1/2013 | Hananouchi et al. |
| 2013/0024580 A1 | 1/2013 | Tsai et al. |
| 2013/0053968 A1 | 2/2013 | Nardini et al. |
| 2013/0110470 A1 | 5/2013 | Vanasse et al. |
| 2013/0110471 A1 | 5/2013 | Lang et al. |
| 2013/0211531 A1 | 8/2013 | Steines et al. |
| 2013/0338673 A1 | 12/2013 | Keppler |
| 2014/0142578 A1 | 5/2014 | Hananouchi et al. |
| 2014/0303938 A1 | 10/2014 | Schoenefeld et al. |
| 2014/0303990 A1 | 10/2014 | Schoenefeld et al. |
| 2014/0371863 A1 | 12/2014 | Vanasse et al. |
| 2015/0052586 A1 | 2/2015 | Mills et al. |
| 2015/0093283 A1 | 4/2015 | Miller et al. |
| 2015/0112348 A1 | 4/2015 | Schoenefeld et al. |
| 2015/0150688 A1 | 6/2015 | Vanasse et al. |
| 2015/0223941 A1 | 8/2015 | Lang |
| 2015/0342739 A1 | 12/2015 | Mahfouz |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0192951 A1 | 7/2016 | Gelaude et al. |
| 2016/0193501 A1 | 7/2016 | Nipper et al. |
| 2016/0270854 A1 | 9/2016 | Chaoui |
| 2016/0296290 A1 | 10/2016 | Furrer et al. |
| 2016/0331467 A1 | 11/2016 | Slamin et al. |
| 2017/0000569 A1 | 1/2017 | Mahfouz |
| 2017/0000614 A1 | 1/2017 | Mahfouz |
| 2017/0027651 A1 | 2/2017 | Esterberg |
| 2017/0035513 A1 | 2/2017 | Mahfouz et al. |
| 2017/0079803 A1 | 3/2017 | Lang |
| 2017/0105841 A1 | 4/2017 | Vanasse et al. |
| 2017/0119531 A1 | 5/2017 | Bojarski et al. |
| 2017/0143499 A1 | 5/2017 | Phipps |
| 2017/0150978 A1 | 6/2017 | Iannotti et al. |
| 2017/0151058 A1 | 6/2017 | Sperling |
| 2017/0273795 A1 | 9/2017 | Neichel et al. |
| 2017/0273801 A1 | 9/2017 | Hodorek |
| 2017/0281357 A1 | 10/2017 | Taylor et al. |
| 2017/0367766 A1 | 12/2017 | Mahfouz |
| 2018/0014835 A1 | 1/2018 | Lo et al. |
| 2018/0161176 A1 | 6/2018 | Vivanz et al. |
| 2018/0233222 A1 | 8/2018 | Daley et al. |
| 2018/0235642 A1 | 8/2018 | Amis et al. |
| 2018/0325526 A1 | 11/2018 | Haddad |
| 2019/0000629 A1 | 1/2019 | Winslow |
| 2019/0015118 A1 | 1/2019 | Neichel et al. |
| 2019/0015221 A1 | 1/2019 | Neichel et al. |
| 2019/0021866 A1 | 1/2019 | Vanasse et al. |
| 2019/0029757 A1 | 1/2019 | Roh et al. |
| 2019/0053851 A1 | 2/2019 | Siemionow et al. |
| 2019/0069913 A1 | 3/2019 | Iannotti et al. |
| 2019/0090952 A1 | 3/2019 | Bonny et al. |
| 2019/0142519 A1 | 5/2019 | Siemionow et al. |
| 2019/0201005 A1 | 7/2019 | Schoenefeld et al. |
| 2019/0269415 A1 | 9/2019 | Lo et al. |
| 2019/0365473 A1 | 12/2019 | Kehres et al. |
| 2020/0030034 A1 | 1/2020 | Kontaxis et al. |
| 2020/0078180 A1 | 3/2020 | Casey |
| 2020/0113632 A1 | 4/2020 | Varadarajan et al. |
| 2020/0155323 A1 | 5/2020 | Lang et al. |
| 2020/0170802 A1 | 6/2020 | Casey |
| 2020/0188121 A1 | 6/2020 | Boux de Casson et al. |
| 2020/0188134 A1 | 6/2020 | Mullen et al. |
| 2020/0246074 A1 | 8/2020 | Lang |
| 2020/0246077 A1 | 8/2020 | Chaoui |
| 2020/0246081 A1 | 8/2020 | Johnson et al. |

(56) References Cited

U.S. PATENT DOCUMENTS

| | | |
|---|---|---|
| 2020/0253740 A1 | 8/2020 | Puncreobutr et al. |
| 2020/0281728 A1 | 9/2020 | Kulper et al. |
| 2020/0330161 A1 | 10/2020 | Chaoui et al. |
| 2020/0405330 A1 | 12/2020 | Bonin, Jr. et al. |
| 2021/0022808 A1 | 1/2021 | Lang |
| 2021/0030477 A1 | 2/2021 | Zuhars et al. |
| 2021/0045888 A1 | 2/2021 | Sbaiz et al. |
| 2021/0068844 A1 | 3/2021 | Lo et al. |
| 2021/0085475 A1 | 3/2021 | Hodorek et al. |
| 2021/0090344 A1 | 3/2021 | Geri et al. |
| 2021/0093388 A1 | 4/2021 | Poltaretskyi et al. |
| 2021/0093389 A1 | 4/2021 | Poltaretskyi et al. |
| 2021/0093390 A1 | 4/2021 | Poltaretskyi et al. |
| 2021/0128179 A1 | 5/2021 | Dupuis et al. |
| 2021/0128244 A1 | 5/2021 | Couture et al. |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0196290 A1 | 7/2021 | Iannotti et al. |
| 2021/0228277 A1 | 7/2021 | Chaoui et al. |
| 2021/0251717 A1 | 8/2021 | Healy et al. |
| 2021/0259844 A1 | 8/2021 | Penninger et al. |
| 2021/0307833 A1 | 10/2021 | Farley et al. |
| 2021/0307911 A1 | 10/2021 | Metcalfe et al. |
| 2021/0315642 A1 | 10/2021 | McGuan et al. |
| 2021/0322130 A1 | 10/2021 | Penney et al. |
| 2021/0327304 A1 | 10/2021 | Buras et al. |
| 2021/0330389 A1 | 10/2021 | Varadarajan et al. |
| 2021/0338337 A1 | 11/2021 | Calloway et al. |
| 2021/0338435 A1 | 11/2021 | Hodorek |
| 2021/0346115 A1 | 11/2021 | Dulin et al. |
| 2021/0361358 A1 | 11/2021 | May et al. |
| 2021/0369353 A1 | 12/2021 | Nikou et al. |
| 2021/0386435 A1 | 12/2021 | Buza et al. |
| 2022/0007006 A1 | 1/2022 | Healy et al. |
| 2022/0008135 A1 | 1/2022 | Frielinghaus et al. |
| 2022/0012949 A1 | 1/2022 | Jones et al. |
| 2022/0020219 A1 | 1/2022 | Chav et al. |
| 2022/0022895 A1 | 1/2022 | Neichel et al. |
| 2022/0031475 A1 | 2/2022 | Deransart et al. |
| 2022/0047278 A1 | 2/2022 | Fitz et al. |
| 2022/0051483 A1 | 2/2022 | Nevins et al. |
| 2022/0051484 A1 | 2/2022 | Jones et al. |
| 2022/0054197 A1 | 2/2022 | Plessers et al. |
| 2022/0071729 A1 | 3/2022 | Healy et al. |
| 2022/0079675 A1 | 3/2022 | Lang |
| 2022/0084298 A1 | 3/2022 | Jones et al. |
| 2022/0087749 A1 | 3/2022 | Marti et al. |
| 2022/0096240 A1 | 3/2022 | Neichel et al. |
| 2022/0110644 A1 | 4/2022 | Gargac et al. |
| 2022/0110685 A1 | 4/2022 | McGuan et al. |
| 2022/0117669 A1 | 4/2022 | Nikou et al. |
| 2022/0125515 A1 | 4/2022 | McGuan et al. |
| 2022/0125519 A1 | 4/2022 | Slagmolen et al. |
| 2022/0148454 A1 | 5/2022 | Jaramaz et al. |
| 2022/0151704 A1 | 5/2022 | Nikou |
| 2022/0151705 A1 | 5/2022 | Nikou et al. |
| 2022/0155854 A1 | 5/2022 | Gibby et al. |
| 2022/0160376 A1 | 5/2022 | Neichel et al. |
| 2022/0160405 A1 | 5/2022 | Casey et al. |
| 2022/0160439 A1 | 5/2022 | Ryan et al. |
| 2022/0168051 A1 | 6/2022 | Ryan et al. |
| 2022/0183757 A1 | 6/2022 | Caldera et al. |
| 2022/0192776 A1 | 6/2022 | Gibby et al. |
| 2022/0202497 A1 | 6/2022 | Janna et al. |
| 2022/0211507 A1 | 7/2022 | Simoes et al. |
| 2022/0218420 A1 | 7/2022 | Qian et al. |
| 2022/0241018 A1 | 8/2022 | Dorman |
| 2022/0249168 A1 | 8/2022 | Besier et al. |
| 2022/0249171 A1 | 8/2022 | Lang |
| 2022/0257321 A1 | 8/2022 | Kehres et al. |
| 2022/0265355 A1 | 8/2022 | Ferrante et al. |
| 2022/0273450 A1 | 9/2022 | Steines et al. |
| 2022/0280249 A1 | 9/2022 | Calloway et al. |
| 2022/0287676 A1 | 9/2022 | Steines et al. |
| 2022/0291741 A1 | 9/2022 | Gibby et al. |
| 2022/0296259 A1 | 9/2022 | Shah |
| 2022/0313386 A1 | 10/2022 | Healy et al. |
| 2022/0313440 A1 | 10/2022 | Metcalfe et al. |
| 2022/0330957 A1 | 10/2022 | Neichel et al. |
| 2022/0338933 A1 | 10/2022 | Metcalfe et al. |
| 2022/0338998 A1 | 10/2022 | Sperling |
| 2022/0346968 A1 | 11/2022 | Pettersson et al. |
| 2022/0346970 A1 | 11/2022 | Nikou |
| 2022/0351828 A1 | 11/2022 | Chaoui |
| 2022/0361955 A1 | 11/2022 | Signoretti et al. |
| 2022/0370142 A1 | 11/2022 | Schoenefeld et al. |
| 2022/0387110 A1 | 12/2022 | Chaoui |
| 2022/0395376 A1 | 12/2022 | Poon et al. |
| 2023/0000556 A1 | 1/2023 | McKinnon et al. |
| 2023/0000570 A1 | 1/2023 | Marti et al. |
| 2023/0000645 A1 | 1/2023 | O'Grady |
| 2023/0018541 A1 | 1/2023 | Tanzer et al. |
| 2023/0038678 A1 | 2/2023 | Lang |
| 2023/0045575 A1 | 2/2023 | Lang et al. |
| 2023/0048940 A1 | 2/2023 | Kontaxis et al. |
| 2023/0056596 A1 | 2/2023 | Farley et al. |
| 2023/0061695 A1 | 3/2023 | Couture et al. |
| 2023/0074630 A1 | 3/2023 | Knopf |
| 2023/0079807 A1 | 3/2023 | Metcalfe et al. |
| 2023/0085093 A1 | 3/2023 | Chaoui et al. |
| 2023/0085387 A1 | 3/2023 | Jones et al. |
| 2023/0109478 A1 | 4/2023 | Chaoui et al. |
| 2023/0139531 A1 | 5/2023 | Roche et al. |
| 2023/0148085 A1 | 5/2023 | Paul et al. |
| 2023/0149099 A1 | 5/2023 | Murphy |
| 2023/0165639 A1 | 6/2023 | Dulin et al. |
| 2023/0165640 A1 | 6/2023 | Dulin et al. |
| 2023/0181257 A1 | 6/2023 | McGuan et al. |
| 2023/0200917 A1 | 6/2023 | Calloway et al. |
| 2023/0248435 A1 | 8/2023 | Bonny et al. |
| 2023/0317298 A1 | 10/2023 | Spanberg et al. |
| 2023/0329791 A1 | 10/2023 | Chaoui et al. |
| 2023/0346397 A1 | 11/2023 | Iannotti et al. |
| 2023/0346480 A1 | 11/2023 | Walch |
| 2023/0355401 A1 | 11/2023 | Metcalfe et al. |
| 2023/0363915 A1 | 11/2023 | Metcalfe et al. |
| 2023/0372018 A1 | 11/2023 | Gangwar et al. |
| 2023/0372111 A1 | 11/2023 | Terrill |

FOREIGN PATENT DOCUMENTS

| | | |
|---|---|---|
| EP | 2471483 A1 | 7/2012 |
| EP | 1858430 B1 | 10/2013 |
| EP | 2670314 B1 | 8/2014 |
| EP | 2244654 B1 | 3/2017 |
| EP | 2770920 B1 | 7/2017 |
| EP | 2770919 B1 | 8/2017 |
| EP | 3248553 A1 | 11/2017 |
| EP | 2303192 B1 | 11/2018 |
| EP | 3125759 B1 | 1/2021 |
| EP | 3760142 A1 | 1/2021 |
| EP | 3845154 A1 | 7/2021 |
| EP | 3861956 A1 | 8/2021 |
| EP | 3996622 A2 | 5/2022 |
| EP | 3481318 B1 | 9/2022 |
| EP | 4103088 A1 | 12/2022 |
| EP | 1323395 A2 | 7/2023 |
| WO | 2005016123 A2 | 2/2005 |
| WO | 2008021494 A2 | 2/2008 |
| WO | 2011110374 A1 | 9/2011 |
| WO | 2012141790 A1 | 10/2012 |
| WO | 2012170376 A2 | 12/2012 |
| WO | 2013060851 A1 | 5/2013 |
| WO | 2013062848 A1 | 5/2013 |
| WO | 2013062851 A1 | 5/2013 |
| WO | 2013142998 A1 | 10/2013 |
| WO | 2014145267 A1 | 9/2014 |
| WO | 2014180972 A2 | 11/2014 |
| WO | 2015018921 A1 | 2/2015 |
| WO | 2015052586 A2 | 4/2015 |
| WO | 2015185219 A1 | 12/2015 |
| WO | 2017091657 A1 | 6/2017 |
| WO | 2017106294 A2 | 6/2017 |

(56) References Cited

FOREIGN PATENT DOCUMENTS

| WO | 2017184792 A1 | 10/2017 |
|---|---|---|
| WO | 2017214537 A1 | 12/2017 |
| WO | 2020104107 A1 | 5/2020 |
| WO | 2020231656 A2 | 11/2020 |
| WO | 2021007418 A2 | 1/2021 |
| WO | 2021026029 A1 | 2/2021 |
| WO | 2021163039 A1 | 8/2021 |
| WO | 2022147591 A1 | 7/2022 |
| WO | 2022169678 A1 | 8/2022 |
| WO | 2023281477 A1 | 1/2023 |
| WO | 2023039032 A1 | 3/2023 |
| WO | 2023086592 A2 | 5/2023 |
| WO | 2023110124 A1 | 6/2023 |
| WO | 2023200562 A1 | 10/2023 |

OTHER PUBLICATIONS

Boissonnat, J.D., "Shape Reconstruction from Planar Cross Sections," Computer Vision, Graphics, and Image Processing, vol. 44, No. 1, Oct. 1988, 29 pp.

Communication pursuant to Article 94(3) EPC from counterpart European Application No. 19209711.1 dated Dec. 21, 2022, 4 pp.

Examination Report No. 1 from counterpart Australian Application No. 2021203700 dated Dec. 1, 2022, 5 pp.

Extended European Search Report issued in connection with corresponding European Patent Application No. 19209711.1; 12 pages, Mar. 23, 2020.

Favre, et al, "Influence of component positioning on impingement in conventional total shoulder arthroplasty" Clinical Biomechanics, Butterworth Scientifics, Nov. 5, 2007, pp. 175-183, vol. 23, No. 2, Guilford, GB.

First Examination Report from counterpart Australian Patent Application No. 2021209349 dated Oct. 6, 2022, 4 pp.

First Examination Report issued in connection with Australian Patent Application No. 2019236759 Jul. 17, 2020, 5 pages.

Gregory, et al, "Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.

International Preliminary Report on Patentability from International Application No. PCT/IB2014/002819, dated Apr. 12, 2016, 12 pp.

International Search Report and Written Opinion of the International Searching Authority issued for PCT Application PCT/IB2014/002819 mailed on May 8, 2015.

Jannotti et al., "Prosthetic positioning in total shoulder arthroplasty," Journal of Shoulder and Elbow Surgery, pp. S111-S121, Jan. 1, 2005, vol. 14, No. 1.

Marker et al., "Contour-Based Surface Reconstruction using Implicit Curve Fitting, and Distance Field Filtering and Interpolation," Volume Graphics, Jan. 2006, 9 pp.

Nguyen et al., "A new segmentation method for MRI images of the shoulder joint," Fourth Canadian Conference on Computer and Robot Vision (CRV'07), May 2007, 8 pp.

Nguyen et al., "Design and Development of a Computer Assisted Glenoid Implantation Technique for Shoulder Replacement Surgery," Computer Aided Surgery, vol. 12, No. 3, May 2007, pp. 152-159.

Notice of Acceptance from counterpart Australian Application No. 2019236759, dated Apr. 27, 2021, 114 pp.

Notice of Acceptance from counterpart Australian Application No. 2021203700, dated Aug. 14, 2023, 41 pp.

Notice of Allowance from counterpart Canadian Application No. 2,927,086, dated Jul. 22, 2021, 1 pp.

Notice of Intent to Grant and Text Intended to Grant from counterpart European Application No. 19209711.1 dated Aug. 26, 2024, 45 pp.

Notice of Intent to Grant from counterpart Australian Application No. 2021209349 dated May 12, 2023, 3 pp.

Office Action issued in connection with Canadian Patent Application No. 2,927,086, Jan. 20, 2021, 3 pages.

Office Action issued in connection with European Patent Application No. 19209711.1, Dec. 22, 2020, 5 pages.

Prosecution History from Australian Patent Application No. 2014333516, dated May 6, 2016 through Oct. 31, 2019, 290 pp. (Uploaded in 5 parts).

Prosecution History from European Patent Application No. 14830864.6, dated Jan. 27, 2015 through Dec. 12, 2019, 307 pp.

Prosecution History from U.S. Appl. No. 15/028,497, dated Apr. 4, 2018 through Apr. 6, 2020, 103 pp.

Prosecution History from U.S. Appl. No. 16/918,347, dated Apr. 29, 2022 through Jul. 24, 2024, 108 pp.

Prosecution History from U.S. Appl. No. 17/229,111, dated Jul. 16, 2021 through Apr. 1, 2022, 53 pp.

Prosecution History from U.S. Appl. No. 17/874,452, dated Nov. 15, 2023 through Aug. 19, 2024, 40 pp.

Prosecution History from U.S. Appl. No. 17/874,472, dated Nov. 15, 2023 through Aug. 19, 2024, 67 pp.

Raaijmakers et al., "A Custom-Made Guide-Wire Positioning Device for Hip Surface Replacement Arthroplasty: Description and First Results," BMC Musculoskeletal Disorders, vol. 11, Jul. 2010, 7 pp.

Response to Communication from counterpart European Application No. 19209711.1, dated Dec. 22, 2020, filed Mar. 24, 2021, 14 pp.

Response to Communication pursuant to Article 94(3) EPC dated Dec. 21, 2022, from counterpart European Application No. 19209711.1 filed Apr. 20, 2023, 25 pp.

Response to European Search Report from counterpart European Application No. 19209711.1, dated Mar. 23, 2020, filed Oct. 22, 2020, 8 pp.

Response to Examination Report No. 1 from counterpart Australian Application No. 2019236759, dated Jul. 17, 2020, filed Dec. 10, 2020, 77 pp.

Response to Office Action dated Dec. 1, 2022, from counterpart Australian Application No. 2021203700 filed Jul. 4, 2023, 80 pp.

Response to Office Action dated Oct. 6, 2022, from counterpart Australian Application No. 2021209349 filed May 5, 2023, 74 pp.

Response to Office Action from counterpart Canadian Application No. 2,927,086, dated Jun. 2, 2020, filed Oct. 2, 2020, 14 pp.

Response to Office Action from counterpart Canadian Application No. 2,927,086, dated Oct. 16, 2019, filed Apr. 16, 2020, 10 pp.

Second Examination Report issued in connection with Australian Patent Application No. 2019236759, Dec. 15, 2020, 4 pages.

U.S. Appl. No. 18/967,458, filed Dec. 3, 2024, by Chaoui et al.

Office Action issued in connection with corresponding Canadian Patent Application No. 2,927,086, Oct. 16, 2019, 7 pages.

Response to Extended Search Report dated Jul. 18, 2025, from counterpart European Application No. 25154176.9 filed Feb. 19, 2026, 15 pp.

* cited by examiner

METHODS, SYSTEMS AND DEVICES FOR PRE-OPERATIVELY PLANNED SHOULDER SURGERY GUIDES AND IMPLANTS

CROSS REFERENCE TO RELATED APPLICATION

This application is a continuation of U.S. application Ser. No. 17/874,452, filed Jul. 27, 2022, which is a divisional of U.S. application Ser. No. 17/229,111, filed Apr. 13, 2021, which is a track one continuation of U.S. application Ser. No. 16/918,347, filed Jul. 1, 2020, which is a divisional of U.S. application Ser. No. 15/028,497, filed Apr. 11, 2016 which is a national stage application under 35 U.S.C. § 371 of PCT Application No. PCT/IB2014/002819, filed Oct. 10, 2014, which claims the benefit of U.S. Provisional Application No. 61/889,213, filed Oct. 10, 2013, the entire contents of each of which are incorporated herein by reference in their entirety.

TECHNICAL FIELD

The presently disclosed subject matter relates to methods, systems and devices for pre-operatively planned shoulder surgery guides and implants. The presently disclosed subject matter also relates to the use of such surgery guides and implants in patients undergoing shoulder surgery.

BACKGROUND

Shoulder replacement is a common surgical operation that has achieved positive results for many patients. Indeed, approximately 10% of joint replacement procedures globally are related to the shoulder. Many shoulder procedures are performed in a patient where substantially normally bone exists for orientation and fixation of a prosthetic replacement, or resurfacing. In these cases, the need for the shoulder replacement can often times be related mostly to the arthritic condition of the joint, and relative absence of healthy cartilage.

In some patients, however, one or more of the bones of the shoulder are not only arthritic, but have also had previous conditions that have caused bone to wear away. In such cases, there may not be sufficient bone to adequately affix a prosthetic implant to the bone, or the bones may have been worn such that the orientation of a joint replacement cannot be satisfactorily determined to ensure a positive patient outcome.

There are a number of factors that complicate the selection, orientation and affixation of prosthetic implant devices, such as glenoid implants and/or humeral implants. Failure to properly account for each factor can lead to improperly sized, misaligned and/or poorly affixed implants that result in a poor surgical outcome for the patient.

In order to increase the likelihood of successful patient outcomes in patients undergoing shoulder surgery, methods, systems and devices are needed that allow for the full understanding and incorporation of all necessary factors for optimization of shoulder implant selection and placement. Thus, a need remains for methods, systems and devices for pre-operatively planned shoulder surgery guides and implants that achieve desired outcomes.

SUMMARY

The presently disclosed subject matter provides methods, systems and devices for pre-operatively planned shoulder surgery guides and implants. The presently disclosed subject matter also provides uses of such surgery guides and implants in patients undergoing shoulder surgery.

An object of the presently disclosed subject matter having been stated hereinabove, and which is achieved in whole or in part by the presently disclosed subject matter, other objects will become evident as the description proceeds when taken in connection with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which.

DETAILED DESCRIPTION

Figure 1A:
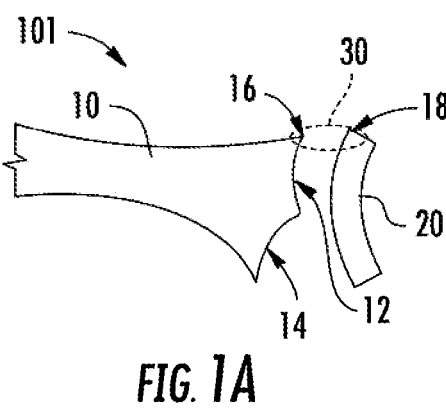
FIG. 1A is a schematic illustration of a step in a pre-operative planning method for designing a shoulder surgery guide where the anterior edge of a glenoid implant is aligned with an anterior edge of a glenoid bone, according to an embodiment of the disclosed subject matter.

Patients requiring shoulder surgery may have one or more of the bones of the shoulder that are not only arthritic, but may also have had previous conditions that have caused bone to wear away. In such cases, there may not be sufficient bone to adequately affix a prosthetic implant to the bone during a routine shoulder surgery. Indeed, the bones may have been worn such that the orientation of a joint replacement cannot be satisfactorily determined to ensure a positive patient outcome.

The glenoid bone can be subject to increased wear due to bone arthritic conditions of the joint, and due to alterations of a normal soft tissue envelope surrounding the joint. In such cases, the orientation of the face of the glenoid portion of the scapula bone may be altered so that the humeral bone is no longer appropriately apposed to the glenoid surface. In the case where the glenoid is severely worn, there can be two or more risks a surgeon must balance in an attempt to improve shoulder function and pain relief.

First, if the optimal orientation of the diseased but treated shoulder is not found and replicated with the prosthesis the patient may experience most operative complications related to subluxation or dislocation of the replaced shoulder joint. This can occur either due to passive inputs to the shoulder (e.g., leaning against it, or lying in bed), or due to active firing of surrounding soft tissue which is not able to be constrained by the replaced joint surfaces.

Additionally, the fixation of a replacement prosthesis, or implant, to the native patient bone can be problematic. Frequently, in order to counteract the risks associated with joint subluxation and dislocation described above, it can be necessary for a surgeon to orient or position the replacement prosthesis or implant in a position better suited to resist imbalanced muscle forces. In such cases, separation forces between the implant and the bone can increase, which in turn can increase the potential for loosening of the joint prosthesis in the bone. Implant loosening can be related to accelerated implant wear, bone erosion, increased tissue inflammation, joint synovitis, and pain.

In patients that have undergone shoulder replacement surgery, range of motion and strength are dependent on shoulder kinematics, which are in turn dependent on a host of factors. Such factor can, for example, include for example implant size, implant position, the design of implant shape, the joint line and soft tissue tension. In some cases it can be difficult to predict optimal implant size and position/orientation using currently available guides and implants. Often times a surgeon finds that there are too many variables to manage at one time. Moreover, the size choices of implants can be limited to the lowest practically functional groups to reduce economic burden to the health care system. Current implant designs and methodologies are inadequate to address these challenges because they are of significant cost, require time to develop, include increased risk of implant failure, and rely on human judgment of potential outcomes post-operatively.

There are many factors that can affect the optimal positioning of shoulder implants during replacement surgery. For example, such factors can include the patient size, relative bone wear, soft tissue strength and condition, six degrees-of-freedom positioning of the glenoid and/or the humeral prosthesis, selected implant size, preoperative patient activity and strength levels, post operative treatment protocols, size and density of patient bone. Additional factors can include patient smoking status, concomitant handicaps and/or patient problems. It can be quite difficult for a surgeon to understand and balance these factors simultaneously. In addition, only a few of these factors are able to be controlled by the surgeon. Finally, each factor does not necessarily have an equally weighted impact on patient outcome. Nevertheless, it is considered that the implant size, position, orientation and bone preparation of the glenoid and the humerus can have a significant impact on the surgical outcomes.

A factor that further complicates, or makes more difficult, a surgeons task of optimally placing a replacement component or implant to counteract these risk is the fact that the condition of the scapula is such that few landmarks exists for the surgeon the comprehend the implant position within the bone. Thus, frequently a surgeon might find that the implant position is not replicating as was envisioned during the surgical intervention.

Others have attempted to improve a surgeon's chance of providing successful patient outcomes by providing operative techniques and tools. What is missing, however, is the ability to fully understand and incorporate multiple factors to optimize the implant selection and placement. Specifically, in some embodiments, the success of the surgery can be highly dependent on both the selection of the matching a prosthesis or prostheses (humeral and/or glenoid), as well as positioning of this prosthesis, as well as the soft tissue status before the surgery. There have been no previous attempts at including these factors in surgical planning and implant design.

Disclosed herein are methods, systems and devices for pre-operatively planned shoulder surgery guides and implants. Methods, systems and devices are provided for the replacement of the shoulder joint, such as the glenohumeral joint, wherein the conditions of the humeral and soft tissue envelop is taken into consideration. More specifically, what is considered is that the shape and position of the glenoid implant is not based solely on what can be seen and measured on the scapula, but can be chosen, designed, planned and placed with incorporation of the same information related to the humerus. After all, the shoulder is a two part joint, i.e. glenoid and humeral head, wherein both parts work in conjunction with one another, and the factors that affect performance of the device can in some embodiments include factors from both sides of the joint.

Appropriate sizing of the prosthesis can be important to successful outcomes, knowing that oversized or "over-stuffed" replacement shoulders are more likely to dislocate, loosen, be painful, and/or have decreased range of motion. Replaced joints where the orientation of the prostheses is improper increases the likelihood of implant dislocation and loosening. Additionally, over-reaming, or too much bone removal, either on the glenoid, or the humerus, can be the cause of implant loosening, "under-stuffing" or inappropriate articular surface placement which can increase pain and decrease range of motion.

Provided herein in some embodiments is a glenoid implant designed and manufactured to specifically match the patient anatomy, including optimal humeral and/or glenoid implant size and shape, and taking into account one or more of the following factors: assessment of the humeral implant fit to the humeral bone; relative hardness of the patient bone preoperatively; height and diameter of the humeral head placed on the humeral stem; orientation, or "offset" of the humeral head; and optimal bone removal for preservation of soft tissue insertion and attachment.

Also provided herein are methods, systems and devices for creation of a shoulder surgery guide based on pre-operative planning which takes into consideration a plurality of factors and assessments. In some embodiments, the creation of a shoulder surgery guide based on pre-operative planning can comprise one or more of the following steps, the combination and order of which can vary: aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting the medialization of the glenoid implant by assessing the volumetric amount of bone needed to be removed by reaming, or the minimum total distance of reaming necessary, in order to optimize the bone to implant interface; analyzing the fixation support in the absence of central pegs that penetrate a vault medially; analyzing the joint line, comprising comparing an original joint line and a new joint line, wherein the new joint line is substantially similar to the original joint line; measuring and matching widths of the glenoid implant and the glenoid bone after reaming and aligning inferior/superior axes of the glenoid implant and bone; assessing and adjusting as needed a thickness/height of the glenoid implant; assessing and adjusting as needed a depth of a glenoid fossa; assessing and adjusting as needed a thickness of a graft; determining a diameter of a humeral head; determining a height of the humeral head; determining a size of humeral bone implant from Houndsfield units measured by an imaging technique (e.g. computed tomography (CT) scan); and/or determining a best fit size of implant from a range of sizes, wherein the range of sizes is selected from the group consisting of length of stem, size of humeral stem, diameter of stem, size diameter of head, height of head, and offset of the center spherical head compared to the center of the face of the humeral stem.

In some embodiments, a pre-operative planning method for designing a shoulder surgery guide is provided for designing a guide for the glenoid. Such a method can be separate from a pre-operative planning method for the humerus, or can in some embodiments be done in conjunction with the planning for the humerus, or humeral side of the joint. Such planning steps particular to the glenoid side of the joint can comprise analysis steps such as those depicted in FIGS. 1A-1I.

For example, a pre-operative planning method for the glenoid can comprise a step 101, as depicted in FIG. 1A, where the anterior edge 18 of glenoid implant 20 can be aligned 30 with anterior edge 16 of glenoid 12 of scapula bone 10 of a patient to be treated. In some embodiments, this step, as with other pre-operative analyses disclosed herein, can be accomplished virtually based on images, e.g. CT images or X-ray images, taken from a subject or patient prior to surgery. By aligning anterior edge 18 of glenoid implant 20 with anterior edge 16 of glenoid 12, data and information can be collected that informs the selection of a glenoid implant and/or supports the creation of a shoulder surgery guide device specific to the patient or subject to be treated.

Figure 1B:
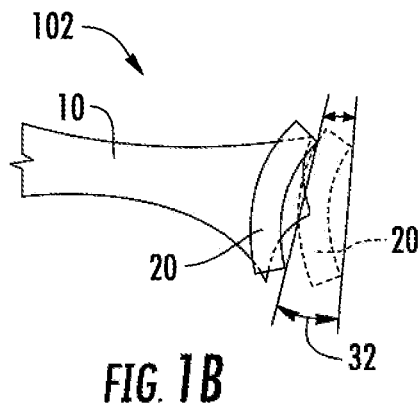
FIG. 1B is a schematic illustration of a step in a pre-operative planning method for designing a shoulder surgery guide where the retroversion of a glenoid implant is adjusted, according to an embodiment of the disclosed subject matter.

In some embodiments, a pre-operative planning method for the glenoid can comprise a step 102, as depicted in FIG. 1B, where the retroversion 32 of glenoid implant 20 is adjusted and/or measured. The retroversion is the placement or degree of posterior rotation of glenoid implant 20 when glenoid 12, including posterior wear 14 (see FIG. 1A), is reamed or otherwise resurfaced to accommodate glenoid implant 20. Such a measurement of retroversion 32 of glenoid implant 20 can be in comparison to the retroversion of the native glenoid in a subject to be treated. In some embodiments, adjusting the retroversion comprises adjusting the retroversion to be about 5 degrees (5°) to about 10 degrees (10°), with a maximum of 10°. In some embodiments, this analysis can be accomplished virtually based on images taken from a subject or patient prior to surgery. By measuring and/or adjusting the retroversion 32 of glenoid implant 20, data and information can be collected that informs the selection of a glenoid implant and/or supports the creation of a shoulder surgery guide device specific to the patient or subject to be treated.

Figure 1C:
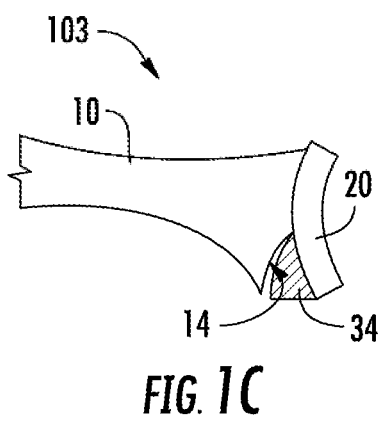
FIG. 1C is a schematic illustration of a step in a pre-operative planning method for designing a shoulder surgery guide where the augmentation of a glenoid implant is adjusted, according to an embodiment of the disclosed subject matter.

In some embodiments, a pre-operative planning method for the glenoid can comprise a step 103, as depicted in FIG. 1C, where a determination can be made as to the necessity of augmentation 34 to support glenoid implant 20. In some embodiments, particularly where glenoid 12 includes posterior wear 14 (or wear at other locations of glenoid 12 not depicted in FIG. 1C), augmentation can be necessary and/or desirable to provide adequate support for the placement and/or attachment of implant 20. Such a step or analysis can in some embodiments comprise adjusting, sizing and/or measuring augmentation 34 needed. In some embodiments, this analysis can be accomplished virtually based on images taken from a subject or patient prior to surgery. By assessing the need for augmentation 34, and/or determining the type and/or size of augmentation 34, data and information can be collected that informs the selection of a glenoid implant and/or supports the creation of a shoulder surgery guide device specific to the patient or subject to be treated.

Figure 1D:
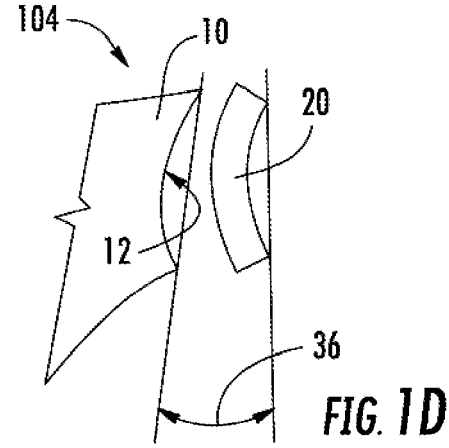
FIG. 1D is a schematic illustration of a step in a pre-operative planning method for designing a shoulder surgery guide where the inferior tilt of a glenoid implant is adjusted, according to an embodiment of the disclosed subject matter.

In some embodiments, a pre-operative planning method for the glenoid can comprise a step 104, as depicted in FIG. 1D, where the inferior tilt 36 of glenoid implant 20 can be measured and/or assessed. Such a measurement of inferior tilt 36 of glenoid implant 20 can be in comparison to the tilt of the native glenoid in a subject to be treated. In some embodiments, this analysis can be accomplished virtually based on images taken from a subject or patient prior to surgery. By assessing the inferior tilt 36 of glenoid implant 20, data and information can be collected that informs the selection of a glenoid implant and/or supports the creation of a shoulder surgery guide device specific to the patient or subject to be treated.

Figure 1E:
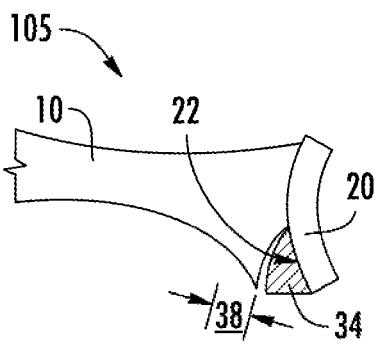
FIG. 1E is a schematic illustration of a step in a pre-operative planning method for designing a shoulder surgery guide where bone support for a glenoid implant is evaluated, according to an embodiment of the disclosed subject matter.

In some embodiments, a pre-operative planning method for the glenoid can comprise a step 105, as depicted in FIG. 1E, where the bone support 38 for glenoid implant 20 can be measured and/or assessed. Such an assessment can in some embodiments comprise characterizing and/or quantifying the amount or degree of bone support 38 for back side 22 of implant 20, taking into consideration posterior wear 14 (see, e.g., FIG. 1A or 1C; or wear at other locations of glenoid 12 not depicted). In some embodiments, this analysis can be accomplished virtually based on images taken from a subject or patient prior to surgery. By assessing the bone support 38, data and information can be collected that informs the selection of a glenoid implant and/or supports the creation of a shoulder surgery guide device specific to the patient or subject to be treated.

Figure 1F:
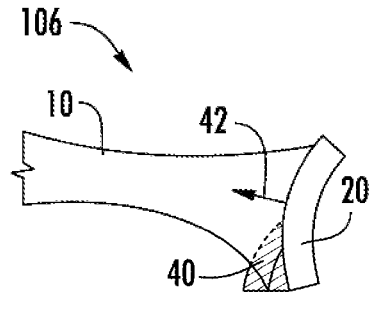
FIG. 1F is a schematic illustration of a step in a pre-operative planning method for designing a shoulder surgery guide where the medialization of a glenoid implant is adjusted by assessing the volumetric amount of bone needed to be removed by reaming, according to an embodiment of the disclosed subject matter.

In some embodiments, a pre-operative planning method for the glenoid can comprise a step 106, as depicted in FIG. 1F, where medialization 42 of glenoid implant 20 can be adjusted and/or characterized by assessing the volumetric amount 40 of bone needed to be removed by reaming. In some embodiments, this analysis can be accomplished virtually based on images taken from a subject or patient prior to surgery. By assessing the bone support 38, data and information can be collected that informs the selection of a glenoid implant and/or supports the creation of a shoulder surgery guide device specific to the patient or subject to be treated.

Figures 1G, 1H:
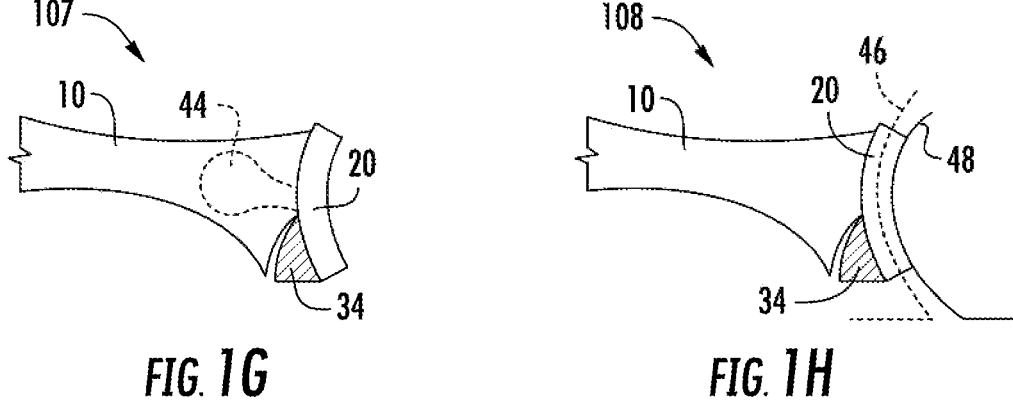
FIG. 1G is a schematic illustration of a step in a pre-operative planning method for designing a shoulder surgery guide where fixation support in the absence of central pegs that penetrate a vault medially is analyzed, according to an embodiment of the disclosed subject matter.
FIG. 1H is a schematic illustration of a step in a pre-operative planning method for designing a shoulder surgery guide where a joint line is analyzed by comparing an original joint line and a new joint line, according to an embodiment of the disclosed subject matter.

In some embodiments, a pre-operative planning method for the glenoid can comprise a step 107, as depicted in FIG. 1G, where fixation support in the absence of a central peg 44 that penetrates a vault medially of scapula 10 can be analyzed. In some embodiments, it is desirable to identify a location on the glenoid for attachment of a prosthesis using a peg or other fixation component without penetrating the anterior wall of the scapula. In some embodiments, this analysis can be accomplished virtually based on images taken from a subject or patient prior to surgery. By assessing the fixation support, data and information can be collected that informs the selection of a glenoid implant and/or supports the creation of a shoulder surgery guide device specific to the patient or subject to be treated.

In some embodiments, a pre-operative planning method for the glenoid can comprise a step 108, as depicted in FIG. 1H, where a joint line can be analyzed by comparing an original joint line 46 with a new joint line 48 as created when implant 20 is affixed to the glenoid surface of scapula 10. The degree to which the joint line changes or shifts, and/or the change in the angle, can be used in optimizing the implant 20 selection and/or placement. In some embodiments, analyzing the joint line, including comparing the original joint line and the new joint line, can comprise analyzing the humeral head lateralization. Humeral head lateralization can comprise the distance the humeral shaft is moved laterally relative to the scapula after the implants are placed. In some embodiments, this analysis can be accomplished virtually based on images taken from a subject or patient prior to surgery. By assessing the joint line, data and information can be collected that informs the selection of a glenoid implant and/or supports the creation of a shoulder surgery guide device specific to the patient or subject to be treated.

Figure 1I:
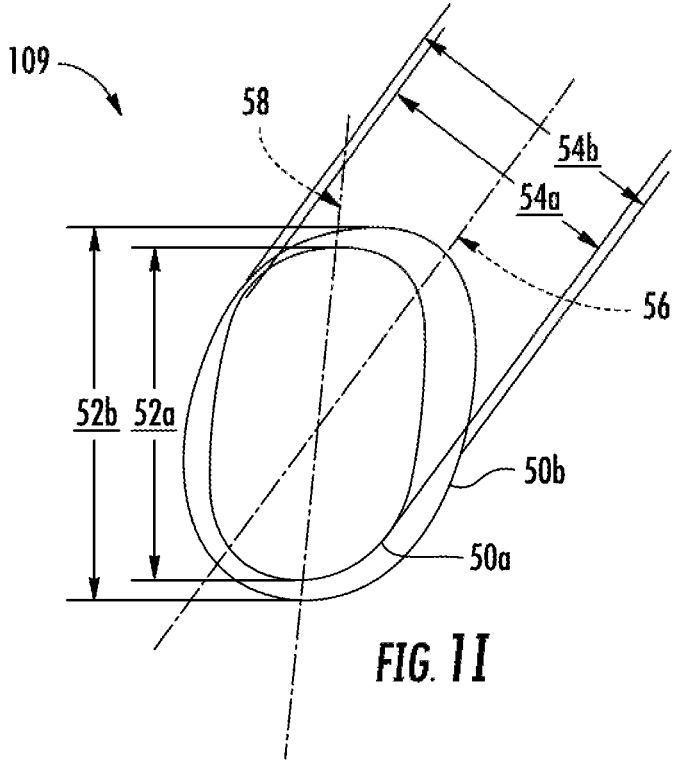
FIG. 1I is a schematic illustration of a step in a pre-operative planning method for designing a shoulder surgery guide where widths of the glenoid implant and the glenoid bone are measured and matched after reaming and aligning inferior and superior axes of the glenoid implant and bone, according to an embodiment of the disclosed subject matter.

In some embodiments, a pre-operative planning method for the glenoid can comprise a step 109, as depicted in FIG. 1I, where the widths of the glenoid implant 50a and the glenoid bone 50b can be measured and matched after reaming and aligning inferior 56 and superior 58 axes of the glenoid implant and bone. Particularly, in some embodiments, a glenoid implant 50a height 52a and width 54a can be measured and aligned with a glenoid bone 50b height 52b and width 54b along inferior 56 and superior 58 axes. In some embodiments, this analysis can be accomplished virtually based on images taken from a subject or patient prior to surgery. By measuring the widths of the glenoid implant 50a and the glenoid bone 50b, and aligning inferior 56 and superior 58 axes of the glenoid implant and bone, data and information can be collected that informs the selection of a glenoid implant and/or supports the creation of a shoulder surgery guide device specific to the patient or subject to be treated.

Such planning steps particular to the glenoid side of the joint can comprise analysis steps such as those depicted in FIGS. 1A-1I, and can comprise all or some of the steps depicted in FIGS. 1A-1I, and in some aspects can be done in any order desired. Alternatively, in some embodiments analysis steps particular to fixation elements can be performed first followed by analysis steps particular to joint articulation.

In some embodiments, a pre-operative planning method for designing a shoulder surgery guide is provided for designed a guide for the humerus, or humeral bone. Such a method can be separate from a pre-operative planning method for the glenoid (discussed above and depicted in FIGS. 1a-1l), or can in some embodiments be done in conjunction with the planning for the glenoid, or glenoid side of the joint. Such planning steps particular to the humerus side of the joint can comprise analysis steps such as those depicted in FIGS. 2A-2D.

Figure 2A:
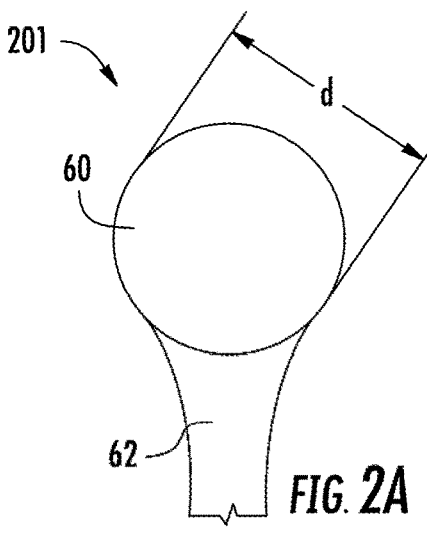
FIG. 2A is a schematic illustration of a step in a pre-operative planning method for designing a shoulder surgery guide where the diameter of a humeral head is determined, according to an embodiment of the disclosed subject matter.

For example, a pre-operative planning method for the humerus can comprise a step 201, as depicted in FIG. 2A, where the diameter d of humeral head 60 of humerus 62 can be measured. In some embodiments, this analysis can be accomplished virtually based on images taken from a subject or patient prior to surgery. By measuring diameter d of humeral head 60, data and information can be collected that informs the selection of a humeral head implant and/or supports the creation of a shoulder surgery guide device specific to the patient or subject to be treated.

Figure 2B:
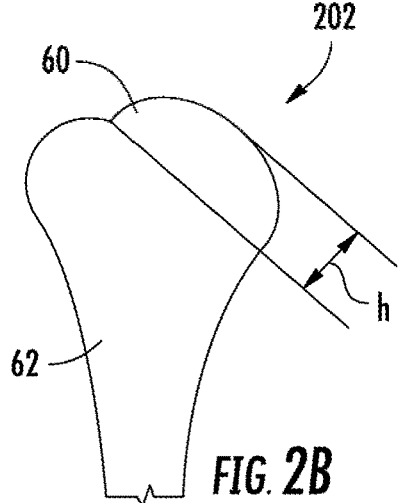
FIG. 2B is a schematic illustration of a step in a pre-operative planning method for designing a shoulder surgery guide where the height of a humeral head is determined, according to an embodiment of the disclosed subject matter.

In some embodiments, a pre-operative planning method for the humerus can comprise a step 202, as depicted in FIG. 2B, where the height h of humeral head 60 of humerus 62 can be measured. In some embodiments, this analysis can be accomplished virtually based on images taken from a subject or patient prior to surgery. By measuring height h of humeral head 60, data and information can be collected that informs the selection of a humeral head implant and/or supports the creation of a shoulder surgery guide device specific to the patient or subject to be treated.

Figure 2C:
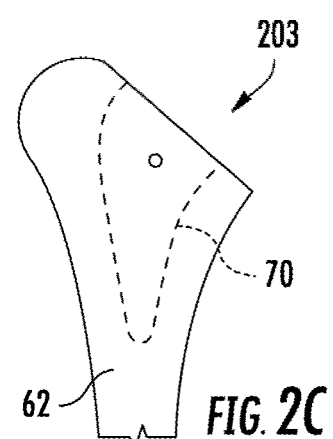
FIG. 2C is a schematic illustration of a step in a pre-operative planning method for designing a shoulder surgery guide where the size of a humeral bone implant from Houndsfield units measured by computed tomography scan is determined, according to an embodiment of the disclosed subject matter.

In some embodiments, a pre-operative planning method for the humerus can comprise a step 203, as depicted in FIG. 2C, where the size of a humeral bone implant stem portion 70 can be determined from Houndsfield units (the Hounsfield scale, named after Sir Godfrey Newbold Hounsfield, is a quantitative scale for describing radiodensity) measured by CT scan. In some embodiments, this analysis can be accomplished virtually based on images taken from a subject or patient prior to surgery. By measuring the size of a humeral bone implant, data and information can be collected that informs the selection of a humeral head implant and/or supports the creation of a shoulder surgery guide device specific to the patient or subject to be treated.

Figure 2D:
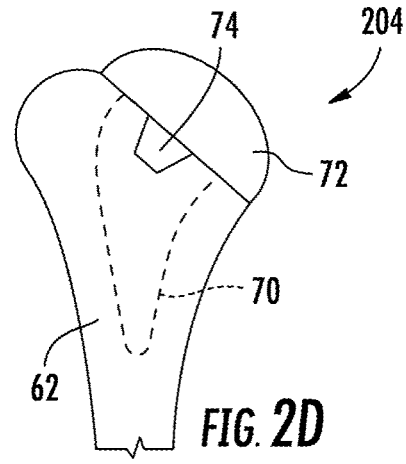
FIG. 2D is a schematic illustration of a step in a pre-operative planning method for designing a shoulder surgery guide where a best fit size of implant from a range of sizes is determined, according to an embodiment of the disclosed subject matter.

In some embodiments, a pre-operative planning method for the humerus can comprise a step 204, as depicted in FIG. 2D, where a best fit size of humeral implant 72 from a range of sizes can be determined. In some embodiments, the range of sizes can be selected from the group consisting of length of stem, size of humeral stem, diameter of stem, size diameter of head, height of head, and offset of the center spherical head compared to the center of the face of the humeral stem. In some embodiments, this analysis can be accomplished virtually based on images taken from a subject or patient prior to surgery. By determining the most appropriate size of humeral implant 72, data and information can be collected that informs the selection of a humeral head implant and/or supports the creation of a shoulder surgery guide device specific to the patient or subject to be treated.

Such planning steps particular to the humeral side of the joint can comprise analysis steps such as those depicted in FIGS. 2A-2D, and can comprise all or some of the steps depicted in FIGS. 2A-2D, and in some aspects can be done in any order desired. Alternatively, in some embodiments analysis steps particular to joint articulation can be performed first followed by analysis steps particular to fixation elements.

Figure 3:
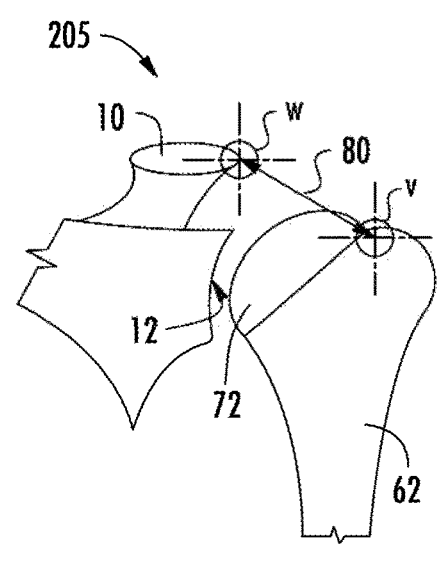
FIG. 3 is a schematic illustration of a step in a pre-operative planning method for designing a shoulder surgery guide where vectors are compared in three dimensions to measure the distance of relocation of humeral tuberosity compared to the scapula, according to an embodiment of the disclosed subject matter.

In some embodiments, a pre-operative planning method for designing a shoulder surgery guide can comprise comparing vectors 80 in three dimensions to measure the distance of relocation of humeral tuberosity 72 compared to the scapula 10, as depicted in analysis 205 in FIG. 3. For example, there are 3 rotator cuff tendons that attach to the proximal humerus in the area of the greater tuberosity and the scapula. Such attachment points are depicted as v and w, respectively, in FIG. 3. These tendons control much of the rotation of the humerus about the scapula as well as having a part in elevating the humerus. If the vector resolved from these 3 tendons changes, kinematics and kinetics of the glenohumeral joint (joint comprising the glenoid and humerus) change. For example, changing the direction of vector 80 can change wear patterns and range of motion (ROM) of the implanted device versus the native joint. Additionally, in some embodiments, changing the magnitude of vector 80 by lengthening or increasing it with a joint prosthesis that is too large for the joint can result in decreased ROM, pain, and increased wear of the prosthetic components. Finally, changing the magnitude of vector 80 by decreasing or shortening it with a joint prosthesis that is too small for the joint can result in an unstable joint that may dislocate and can result in suboptimal mechanics for elevating the humerus. In some embodiments, this analysis can be accomplished virtually based on images taken from a subject or patient prior to surgery. By comparing vector 80 in three dimensions to measure the distance of relocation of humeral tuberosity 72 compared to the scapula 10, data and information can be collected that informs the selection of a humeral head implant, glenoid implant, and/or supports the creation of a shoulder surgery guide device specific to the patient or subject to be treated.

Figure 4:
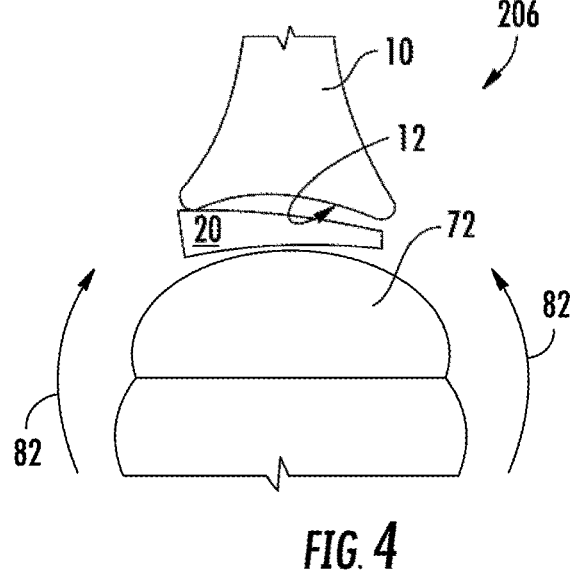
FIG. 4 is a schematic illustration of a step in a pre-operative planning method for designing a shoulder surgery guide where range of motion analysis is conducted, including virtually positioning implants through extreme ranges of motion to measure impact locations and compensate for necessary functional range of motion, according to an embodiment of the disclosed subject matter.

In some embodiments, a pre-operative planning method designing a shoulder surgery guide can comprise a step 206, as depicted in FIG. 4, where range of motion (ROM) analysis 82 can be conducted, including virtually positioning implants 20, 72 through extreme ranges of motion to measure impact locations and compensate for necessary functional ROM. In some embodiments, this analysis can be accomplished virtually based on images taken from a subject or patient prior to surgery. By measuring the ROM with respect to glenoid implants 20 and/or humeral implants 72, data and information can be collected that informs the selection of glenoid implant, a humeral head implant and/or supports the creation of a shoulder surgery guide device specific to the patient or subject to be treated.

Figure 5:
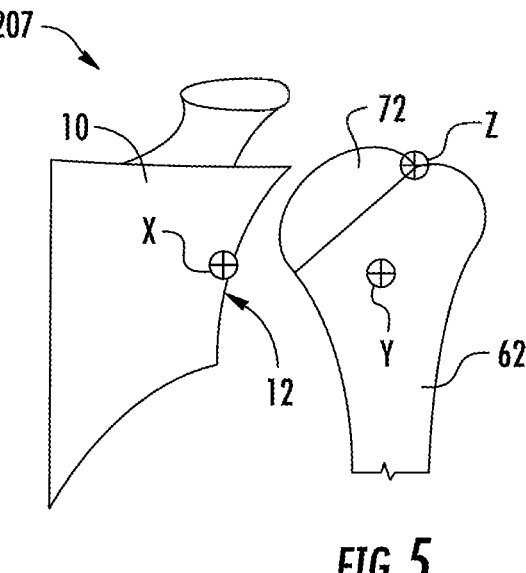
FIG. 5 is a schematic illustration of a step in a pre-operative planning method for designing a shoulder surgery guide where soft tissue analysis comprising determining key soft tissue insertion points is conducted, according to an embodiment of the disclosed subject matter.

In some embodiments, a pre-operative planning method designing a shoulder surgery guide can comprise a step 207, as depicted in FIG. 5, where soft tissue, e.g. muscle, analysis is conducted. In some aspects, soft tissue analysis can comprise determining and/or assessing soft tissue insertion points (e.g., X, Y and Z) and analyzing impacts on and/or impacts from use of one or more implants (glenoid and/or humeral). In some embodiments, four rotator cuff muscles and their attachments points can be analyzed. For example, in some aspects analysis can comprise the subscapularis that attaches at an attachment point Y near the lesser tuberosity and at an attachment point X near the anterior glenoid. In some aspects analysis can comprise the supraspinatus that attaches at an attachment point Z near the anterior greater tuberosity and above the scapular spine (shoulder blade; not shown). In some aspects, soft tissue analysis can comprise the infraspinatus that attaches at the greater tuberosity (posterior to supraspinatus) and below the scapular spine (posterior). In some aspects, soft tissue analysis can comprise the teres minor that attaches posterior on the humerus and on the inferior scapular boder. In some embodiments, this analysis can be accomplished virtually based on images taken from a subject or patient prior to surgery. By analyzing the soft tissue around the glenohumeral joint, data and information can be collected that informs the selection of a glenoid implant, a humeral head implant and/or supports the creation of a shoulder surgery guide device specific to the patient or subject to be treated.

In some embodiments, the disclosed pre-operative planning methods can further comprise designing a shoulder surgery guide device based upon parameters collected from the planning methods and analyses. In some embodiments, a designed shoulder surgery guide can be produced, wherein the produced surgery guide is configured in accordance with parameters collected from the planning and analysis specific to the patient to be treated. In some aspects, a guide, and/or a prosthetic implant, can be produced or made using a three dimensional (3D) printing device. In some embodiments, a shoulder surgery guide device produced as disclosed herein can comprise a polymeric or metallic material.

In some embodiments, the disclosed pre-operative planning methods can further comprise identifying a prosthetic shoulder implant, and/or identifying a placement position for the prosthetic shoulder implant. The identification of a prosthetic shoulder implant and placement position takes into consideration at least one of the factors selected from the group consisting of adjustments in glenoid implant size, augmentation depth, augment position, positioning in six degrees of freedom, fixation type, fixation size, reaming depth, reaming diameter, reaming angle, and/or a combination thereof. The above method can further comprise a step of recommending implants and placement positions, with recommended adjustments in humerus stem size, length, head diameter, head height, head offset and rotation (axial). A prosthetic shoulder implant can in some embodiments comprise a glenoid implant.

In some embodiments, the above methods of creating a shoulder surgery guide based on pre-operative planning can further comprise one or more optimization steps. Such optimization steps can comprise the identification of procedural risks based on measurements of one or more of a plurality of factors. Such factors can in some embodiments comprise whether the glenoid face coverage is maximized (e.g. about 0 to about 2 mm), the overhang of the glenoid face is minimized (e.g. about 0 to about 3 mm), and/or the bone removal on the glenoid face is minimized, such as for example less than about 2 mm of depth. Continuing, in some embodiments such optimization factors can comprise whether the glenoid retroversion is less than about 5 degrees to about 10 degrees, the seating of the glenoid implant is greater than about 80%, i.e. about 80% of the back side of the glenoid implant is supported by or touching bone, whether there is minimized penetration of the glenoid cortical wall anteriorly (e.g. about 0 mm to about 3 mm), and/or the depth of any glenoid implant augment feature is as minimal as possible. Still yet, in some embodiments such optimization factors can comprise whether there is less than about 1 mm of difference between the anatomic joint line and the new joint line with implants, there is minimized penetration of the glenoid cortical wall anteriorly, and/or there is maximized bone thickness behind the glenoid, preferably greater than 3 mm. In some embodiments such optimization factors can comprise whether the orientation offset between the native glenoid and implant superior/inferior axis is minimized, preferably less than 5 degrees, the superior or inferior tilt versus native glenoid is minimized, preferably less than 5 degrees, there is less than about 5% to about 10% change in soft tissue length at extreme ranges of motion, there is maximized filing of the humeral metaphysis, in some embodiments greater than about 90% of metaphyseal bone filled based on and identification of metaphyseal bone by use of Houndsfield units, there is an absence of a humeral head overhang compared to the cut, or prepared surface of the humeral bone, there is minimal difference in humeral head diameter between anatomic and implant, in some embodiments less than about 3 mm, there is minimal difference in humeral head height between anatomic and implant, in some embodiments less than about 1 mm, and/or there is greater tuberosity to medial head edge comparison to anatomic, in some embodiments less than about 2 mm. In some embodiments, such procedural risks (any and/or all from the above list) can be determined virtually based on images taken from a subject prior to surgery.

Figure 6:
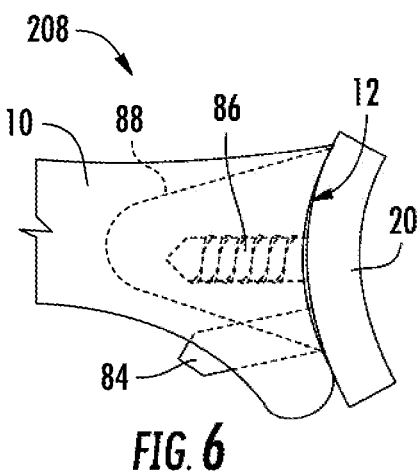
FIG. 6 is a schematic illustration of a step in a pre-operative planning method for designing a shoulder surgery guide where penetration of the cortical wall anteriorly of the vault is assessed, according to an embodiment of the disclosed subject matter.

With respect to the above optimization steps that comprise the identification of procedural risks, in some embodiments the penetration of the cortical wall anteriorly of the vault can be assessed, as depicted in FIG. 6. FIG. 6 depicts step 208 of assessing the penetration of the cortical wall anteriorly of the vault 88 by a support structure 84 of glenoid implant 20. In some embodiments, an additional or alternate support structure 86 can be used to affix implant 20 to glenoid 12.

Figure 7:
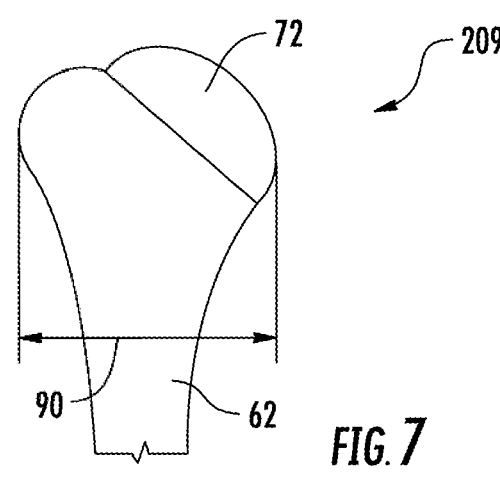
FIG. 7 is a schematic illustration of a step in a pre-operative planning method for designing a shoulder surgery guide where the width of the greater tuberosity to medial head edge with an implant is compared to the anatomic width, according to an embodiment of the disclosed subject matter.

Also with respect to the above optimization steps that comprise the identification of procedural risks, in some embodiments the width of the greater tuberosity to medial head edge with an implant can be compared to the anatomic width. For example, in FIG. 7 the width 90 of the greater tuberosity to medial head edge with an implant 72 can be compared to the width of the anatomical humeral head.

In some aspects, the planning methods and analysis steps disclosed herein can be done pre-operatively. That is, they can be done prior to surgery in a virtual or software-based environment. Such virtual simulations can in some embodiments be based on images or scans taken from a subject prior to surgery. Currently available and future imaging techniques, e.g. computed tomography (CT), x-ray imaging, positron emission tomography (PET), ultrasound, etc., can be used to capture images and data to be used in simulation-based analysis and planning to identify suitable prosthetic implants and/or design surgery guides. By using images captured from a subject or patient to be treated, the analysis and results can be specific to the subject or patient and can take into consideration the particularities of that subject's condition.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As such, in some embodiments the disclosed pre-operative planning methods can further comprise providing a computer readable medium having stored thereon executable instructions that when executed by the processor of a computer control the computer to perform one or more of the planning method and/or analysis steps. For example, in some embodiments computer readable medium can have stored thereon executable instructions that when executed by the processor of a computer can control the computer to generate a virtual 3D model of a glenoid guide device reflecting one or more optimized parameters determined during pre-operative planning. Additionally, in some aspects, computer readable medium can have stored thereon executable instructions that when executed by the processor of a computer control the computer to control a 3D printing device in communication with the computer, whereby the 3D printing device can print a glenoid guide device or humeral guide device for use in shoulder replacement surgery in a patient for which pre-operative planning method steps were conducted.

Further, in some aspects of the disclosed methods, systems and devices, a computer readable medium can be provided having stored thereon executable instructions that when executed by a processor of a computer can control the computer to generate a virtual 3D model of a glenoid implant device reflecting one or more optimized parameters determined during pre-operative planning. Thus, in some embodiments a computer readable medium is provided, wherein the computer readable medium has stored thereon executable instructions that when executed by the processor of a computer control the computer to perform one or more of the planning method and/or analysis steps as disclosed herein.

It should be noted that the computers, computing devices, hardware and/or functionality described herein may constitute a special purpose test device. Further, computers, computing devices, hardware and/or functionality described herein can improve the technological field of pre-operative planning for shoulder surgery and can improve generation of virtual modeling systems.

The subject matter described herein for generating 3D models of glenoid and/or humeral implant devices, and/or for modeling and virtually simulating pre-operative shoulder surgery analysis improves the likelihood of a positive outcome from shoulder surgery. It should also be noted that a computing platform, computer, computing device, and/or hardware that implements the subject matter described herein may comprise a special purpose computing device usable to generate 3D models of glenoid and/or humeral implant devices, and/or for modeling and virtually simulating pre-operative shoulder surgery analysis.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments a computer readable medium is provided, having stored thereon executable instructions that when executed by the processor of a computer control the computer to perform steps comprising generating a virtual three dimensional model of a glenoid and/or humeral guide reflecting one or more optimized parameters determined during pre-operative planning based on the above method steps. In some embodiments, a computer readable medium is provided, having stored thereon executable instructions that when executed by the processor of a computer control a 3D printing device in communication with the computer, whereby the 3D printing device prints a glenoid and/or humeral guide for use in shoulder replacement surgery in a patient for which the optimization analysis was conducted.

Figure 8:
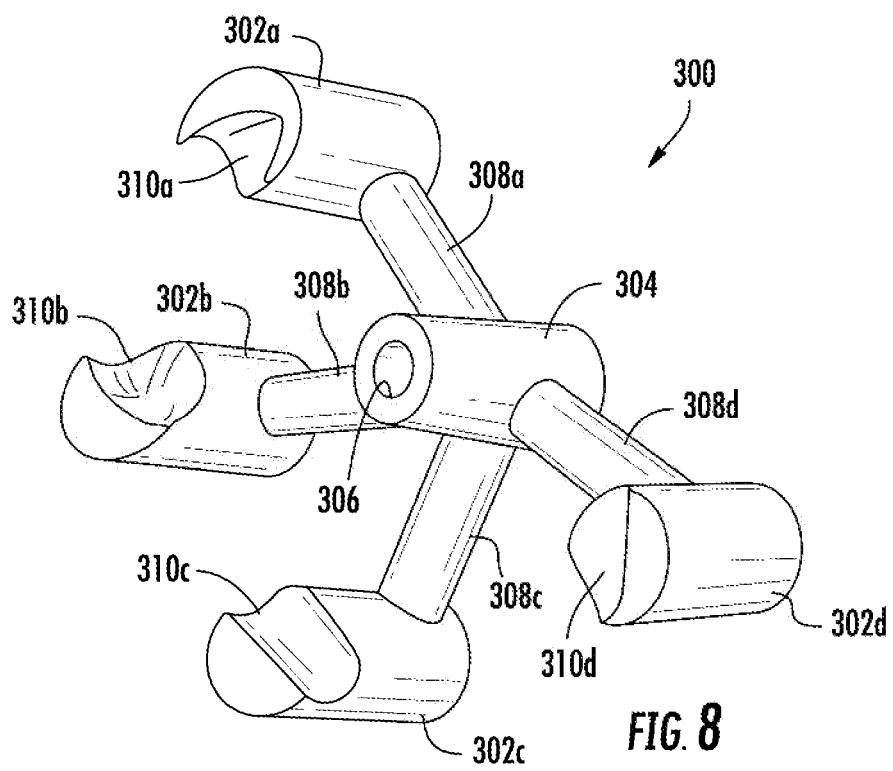
FIGS. 8 and 9 are rear and front perspective views, respectively, of a shoulder surgery guide, according to an embodiment of the disclosed subject matter.
Figure 9:
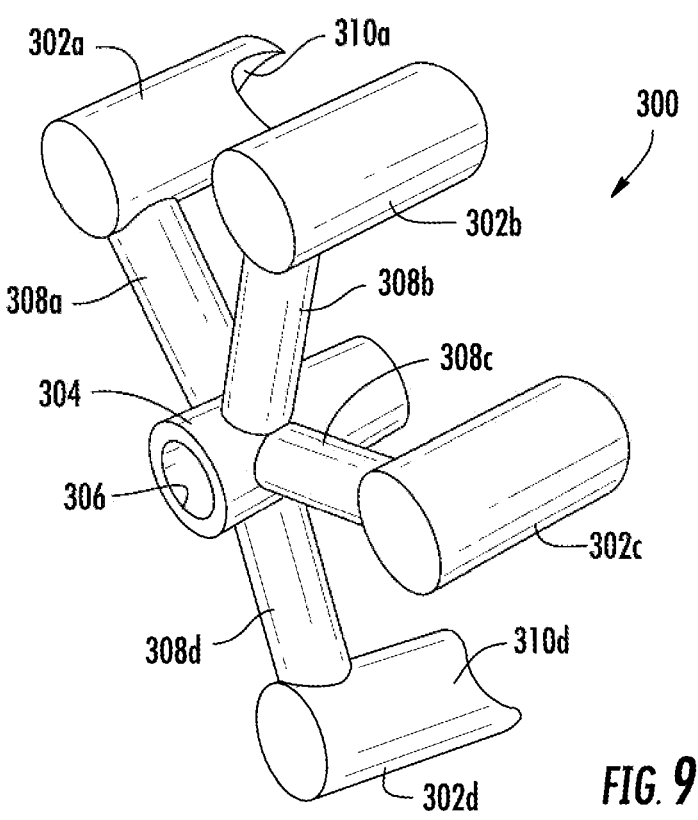
Figure 10:
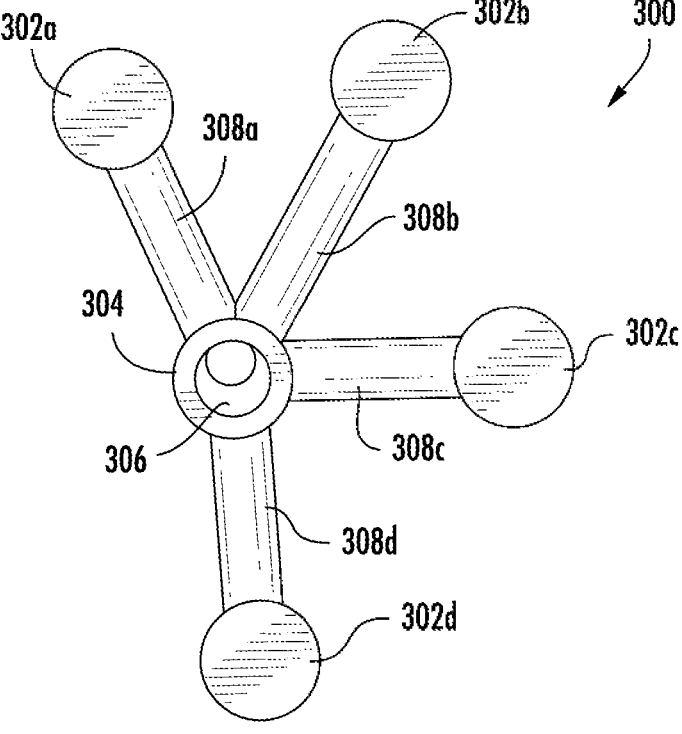
FIG. 10 is a plan view a shoulder surgery guide, according to an embodiment of the disclosed subject matter.
Figure 11:
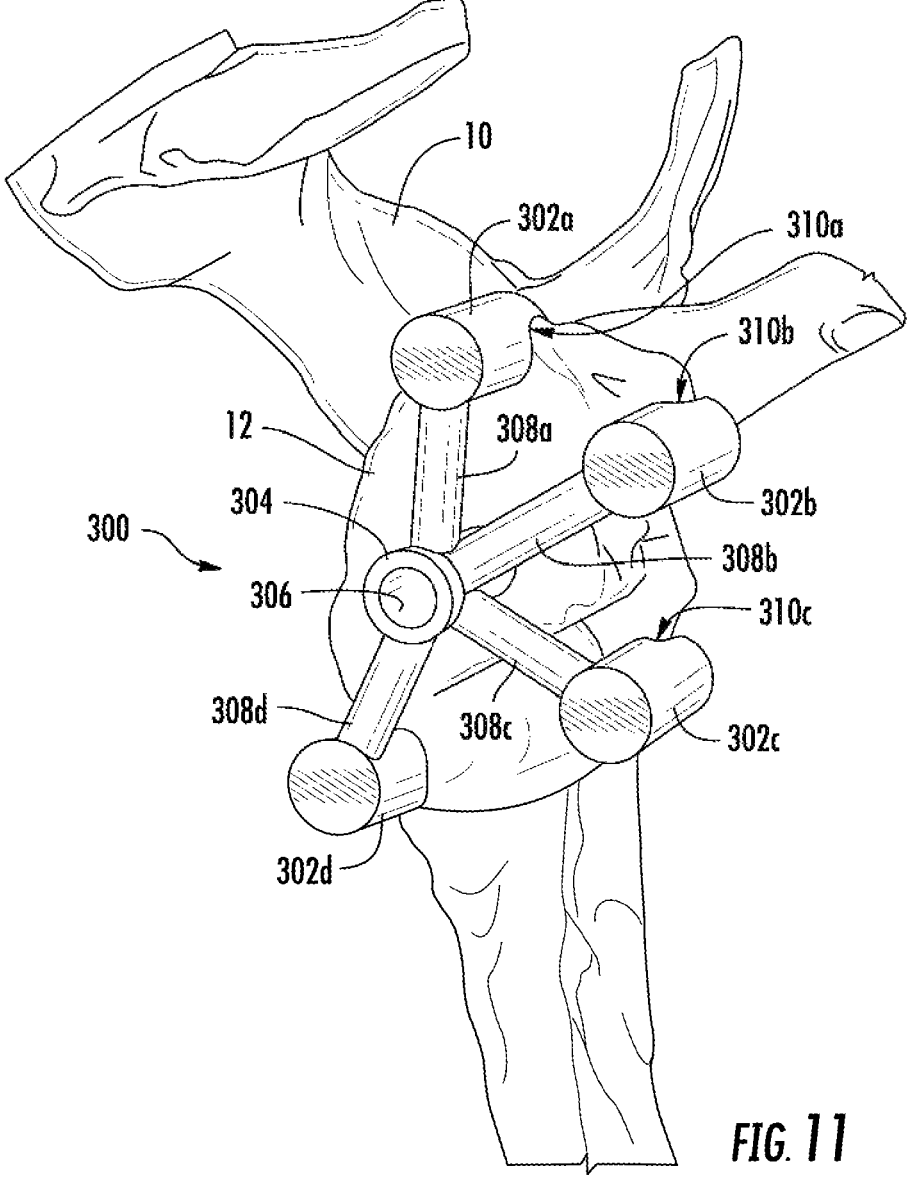
FIG. 11 is a perspective view of a shoulder surgery guide as used during shoulder surgery on a glenoid surface of a scapula, according to an embodiment of the disclosed subject matter.

Based on the pre-operative planning steps and analyses disclosed herein, in some embodiments shoulder surgery guides or guide devices can be designed, simulated and in some instances produced for use in shoulder replacement surgery. Such a surgery guide device is depicted in FIGS. 8-11. FIGS. 8 and 9 are rear and front perspective views, respectively, of a shoulder surgery guide, while FIG. 10 is a plan view of a shoulder surgery guide. As depicted in FIGS. 8-10, shoulder surgery guide 300 can in some embodiments comprise a plurality of peripheral guide structures 302 configured to align with the edge or rim of the glenoid face. In FIGS. 9-11 four peripheral guide structures 302, namely 302a, 302b, 302c, and 302d, are shown, but any number of peripheral guide structures 302, including for example 2, 3, 4, 5, 6, 7, 8, 9 or 10, could be used so long as there are a sufficient number to align and stabilize guide 300 on a glenoid face (see FIG. 11 for a depiction of the guide in use). In some embodiments, peripheral guide structures 302a, 302b, 302c, and 302d can each comprise a corresponding indentation or cupped surface 310a, 310b, 310c, and 310d that can be configured to wrap over the edge of the rim of the glenoid. Cupped surface 310a, 310b, 310c, and 310d can secure and stabilize guide 300 at the desired and predetermined (based on the pre-operative analysis and guide design) location on the glenoid. In some embodiments, some peripheral guide structures may not include a cupped surface, or may include a different shaped structure, as needed to accommodate and align with a given point along the edge of a glenoid. Each peripheral guide structure 302, and corresponding cupped surface 310, can be predetermined and configured based on individual datum points collected during a pre-operative analysis and guide design, as disclosed herein.

Peripheral guide structures 302a, 302b, 302c, and 302d generally extend radially from a hub structure 304, and can be positioned and secured to hub structure 304 by radial arms 308a, 308b, 308c, and 308d. Of course, the number of radial arms 308 will be dictated by, and correspond to, the number of peripheral guide structures 302. The length of radial arms 308 can be determined and configured based on individual datum points collected during a pre-operative analysis and guide design, as disclosed herein, such that each of the peripheral guide structures 302 align with the rim of the glenoid at the desired location.

Hub structure 304 can comprise a central port 306 comprising a cylindrical opening extending through the entire length (see front view FIG. 8, rear view FIG. 9, and plan view FIG. 10) of hub structure 304 and providing an opening through which a pin, drill or boing device can be guided to create an opening, i.e. drill a hole, and/or place a guide pin in the glenoid face. With peripheral guide structures 302a, 302b, 302c, and 302d aligning with the rim or edge of the glenoid, hub structure 304, by virtue of its attachment to each of peripheral guide structures 302a, 302b, 302c, and 302d, can be aligned at the predetermined and desired location on the face of a glenoid. The location of hub structure 304, and particularly central port 306, can be predetermined and configured based on pre-operative analysis such that central port 306 provides a steady and secure guide to the location on the glenoid where a prosthesis or implant is to be attached.

FIG. 11 depicts shoulder surgery guide 300 in use, or aligned with the face of glenoid 12 on scapula 10. Cupped surface 310a, 310b, 310c, and 310d wrap over the edge of the rim of the glenoid 12 such that guide 300 is aligned with and stabilized over glenoid 12. With guide 300 in place on glenoid 12, a pin, drill or boing device can be inserted into central port 306, which can guide the pin, drill or boing device to the precise location on glenoid 12 where a predetermined attachment point is located based on pre-operative analytics.

In some embodiments, a hybrid patient specific implant can be provided, in some embodiments a humeral implant, wherein the hybrid implant can comprise a fixation component and an articular component. The hybrid patient specific implant can comprise a standardized range of fixation components for securing the implant to the humerus. Such fixation component can comprise a stem comprising varying sizes, materials, coatings and surface treatments.

In some embodiments, an intermediate holder can be provided for securing the articular component to the fixation component. Such intermediate holder can vary in size, can comprise standardized materials and coatings, and can comprise a standardized connection between the fixation component, e.g. stem, and holder. Such standardized connection can comprise threads, interlocking components, morse taper connections, snap fit connections (whether using snap rings or not), and the like.

In some aspects, the customized patient specific articular component can comprise a desired articular shape and/or position based on the methods of analysis and optimization disclosed herein. By way of example and not limitation, the shape and position of the articular component can be centered or offset, and can have varying degrees of depth.

In some aspects, the articular component can comprise a desired range of motion blockage. Range of motion tests with virtual pre-operative planning as discussed herein can reveal potential impingement of humeral polyethylene on scapula bone, or humeral tuberosities on acromion. In some aspects, an analysis comparing predicted range of motion based on necessary activities of daily living can be conducted. In some embodiments, a further step can include resolving any conflicts between impingement and activities of daily living needs. Taking these factors into consideration, the articular component shape and placement can then be optimized.

Additionally, in some embodiments, the articular component shape can be adjusted. Such variations, based in some aspects on pre-operative planning as discussed herein, can comprise variations in radial location, depth/magnitude and/or angle.

In some embodiments, methods of treating a patient, and/or surgical methods, are provided wherein one or more of the disclosed methods of analysis and optimization are performed on a patient in need of shoulder or other joint surgery. In some embodiments, methods of treating a patient are provided wherein a disclosed method of analysis and optimization is performed, an optimized guide is designed and created, and one or more glenoid and/or humeral implants are designed, created, and/or selected. In some embodiments, a method of treating a patient can comprise utilizing the pre-operative planning to design and optimize a guide and one or more glenoid and/or humeral implants, and the use of the guide to surgically implant the one or more glenoid and/or humeral prosthetic devices.

In some embodiments, a kit is provided wherein the kit can comprise a set of instructions for performing the disclosed pre-operative planning methods and analyses. Such a kit can further comprise one or more glenoid and/or humeral prosthetic devices, wherein the devices can be customizable or modular in design such that the prosthetic device can be optimized for the patient based on the pre-operative planning analysis. In some embodiments, a kit can further comprise a guide for placing a prosthetic device during shoulder surgery, wherein the guide can be optimized for the patient based on the pre-operative planning analysis. In some embodiments, a kit can further comprise a 3-D printing device for producing a guide and/or one or more glenoid and/or humeral prosthetic devices. In some embodiments, a kit can further comprise a computer-readable medium (software) for use in conducting the pre-operative planning, and designing a guide, glenoid implant and/or humeral implant based on input parameters gathered during the disclosed methods of analysis.

In some embodiments a patient can comprise a mammalian subject. In some embodiments, the patient can be a human subject, including an adult, adolescent or child.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A computer-implemented pre-operative planning method for designing a shoulder surgery guide, the method comprising identifying, with processing circuitry of a computing device, procedural risks, wherein identifying procedural risks comprises determining:

whether coverage of a glenoid face of a glenoid by an implant is maximized;

whether an overhang of the glenoid face is minimized;

whether bone removal on the glenoid face is minimized;

whether a glenoid retroversion of the glenoid is less than about 5 to about 10 degrees;

whether seating of the implant is greater than about 80% of an implant coverage area;

whether there is minimized anteriorly penetration of a glenoid cortical wall of the glenoid;

whether a superior or inferior tilt of the glenoid post-operation would be less than 5 degrees relative to a superior or inferior tilt of the glenoid pre-operation; and generating, with the processing circuitry of the computing device, information for designing the shoulder surgery guide based on the identified procedural risks.

2. The method of claim 1, wherein identifying, with the processing circuitry of the computing device, the procedural risks further comprises determining, with the processing circuitry of the computing device, whether there is greater than about 3 mm bone thickness behind the glenoid.

3. The method of claim 1, wherein identifying, with the processing circuitry of the computing device, the procedural risks further comprises determining, with the processing circuitry of the computing device, whether an orientation offset between the glenoid and a superior/inferior axis of the implant is less than about 5 degrees.

4. The method of claim 1, wherein identifying, with the processing circuitry of the computing device, the procedural risks further comprises determining, with the processing circuitry of the computing device, whether there is an absence of a humeral head overhang compared to a cut or prepared surface of a humeral bone.

5. The method of claim 1, wherein identifying, with the processing circuitry of the computing device, the procedural risks further comprises determining, with the processing circuitry of the computing device, whether a difference between a diameter of a humeral head of a humerus of a subject and a diameter of a humeral head of the implant is less than about 3 mm.

6. The method of claim 1, wherein identifying, with the processing circuitry of the computing device, the procedural risks further comprises determining, with the processing circuitry of the computing device, whether a difference between a diameter of a humeral head of a humerus of a subject and a diameter of a humeral head of the implant is less than about 1 mm.

7. The method of claim 1, wherein identifying, with the processing circuitry of the computing device, the procedural risks comprises identifying, with the processing circuitry of the computing device, the procedural risks virtually based on images taken from a subject prior to surgery.

8. The method of claim 1, further comprising determining, with the processing circuitry of the computing device, whether a depth of any glenoid implant augment feature of the glenoid implant is as minimal as possible.

9. The method of claim 1, wherein identifying, with the processing circuitry of the computing device, the procedural risks comprises determining, with the processing circuitry of the computing device, whether there is less than about 5% to about 10% change in soft tissue length at extreme ranges of motion when the glenoid implant is implanted.

* * * * *